United States Patent
Quan et al.

(10) Patent No.: US 6,965,036 B2
(45) Date of Patent: Nov. 15, 2005

(54) INTERMEDIATES FOR GUANIDINE MIMICS AS FACTOR XA INHIBITORS

(75) Inventors: Mimi L. Quan, Yardley, PA (US); Renhua Li, Noblesville, IN (US)

(73) Assignee: Bristol-Myers Squibb Pharma Company

(*) Notice: Subject to any disclaimer, the term of this patent is extended or adjusted under 35 U.S.C. 154(b) by 259 days.

(21) Appl. No.: 10/602,214

(22) Filed: Jun. 24, 2003

(65) Prior Publication Data

US 2004/0063772 A1 Apr. 1, 2004

Related U.S. Application Data

(62) Division of application No. 09/924,381, filed on Aug. 8, 2001, which is a division of application No. 09/099,358, filed on Jun. 18, 1998, now Pat. No. 6,339,099.
(60) Provisional application No. 60/050,265, filed on Jun. 20, 1997.

(51) Int. Cl.⁷ ............... C07D 401/04; C07D 413/04; C07D 261/20; C07D 231/14; C07D 401/14
(52) U.S. Cl. ................. 548/335.5; 548/356.1; 548/365.7
(58) Field of Search ............ 548/335.5, 356.1, 548/365.7

(56) References Cited

U.S. PATENT DOCUMENTS

| | | | |
|---|---|---|---|
| 5,202,330 A | 4/1993 | Atwal et al. ............ | 514/274 |
| 5,317,103 A | 5/1994 | Baker et al. ............ | 544/367 |
| 5,342,851 A | 8/1994 | Sanfilippo et al. ...... | 514/370 |
| 5,463,071 A | 10/1995 | Himmelsbach et al. .. | 548/281 |
| 5,616,601 A | 4/1997 | Khanna et al. .......... | 514/399 |
| 5,681,838 A | 10/1997 | Zoller et al. ............ | 514/307 |
| 5,707,998 A | 1/1998 | Takase et al. ........... | 514/259 |
| 6,020,357 A | 2/2000 | Pinto et al. ............. | 514/406 |

FOREIGN PATENT DOCUMENTS

| | | |
|---|---|---|
| EP | 234830 A | 9/1987 |
| EP | 236902 A | 9/1987 |
| EP | 513387 B | 11/1992 |
| EP | 554829 A | 8/1993 |
| JP | 4247081 A | 9/1992 |
| WO | WO 9402477 A | 2/1994 |
| WO | WO 9514683 A | 6/1995 |
| WO | WO 9518111 A | 7/1995 |
| WO | WO 9628427 A | 9/1996 |
| WO | WO 9640143 A | 12/1996 |
| WO | WO 9723212 A | 7/1997 |
| WO | WO 9732583 A | 9/1997 |
| WO | 98-57951 | * 12/1998 |

OTHER PUBLICATIONS

Tidwell et al. "Diarylamidine derivatives with one or both of the aryl moieties consisting of an indole or indole–like ring, inhibitors of arginine–specific esteroproteases". J. Med. Chem. (1978), 21(7), 613–623.

* cited by examiner

*Primary Examiner*—James O. Wilson
*Assistant Examiner*—Tamthom N. Truong
(74) *Attorney, Agent, or Firm*—Jing G. Sun; David H. Vance

(57) ABSTRACT

The present application describes intermediates for nitrogen containing heteroaromatics and derivatives thereof of formula I:

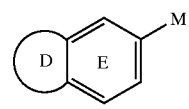

or pharmaceutically acceptable salt forms thereof, wherein rings D—E represent guanidine mimics, which are useful as inhibitors of factor Xa.

3 Claims, No Drawings

INTERMEDIATES FOR GUANIDINE MIMICS AS FACTOR XA INHIBITORS

CROSS-REFERENCE TO RELATED APPLICATIONS

This application is a Continuation of U.S. application Ser. No. 09/924,381, filed Aug. 8, 2001 and allowed; which is a divisional of U.S. application Ser. No. 09/099,358, filed Jun. 18, 1998 and issued as U.S. Pat. No. 6,339,099; which in turn claims the priority benefit of U.S. Provisional Application No. 60/050,265, filed Jun. 20, 1997 and now abandoned; all of which are incorporated herein by reference.

FIELD OF THE INVENTION

This invention relates generally to novel intermediates for guanidine mimics which are inhibitors of trypsin-like serine protease enzymes, especially factor Xa, pharmaceutical compositions containing the same, and methods of using the same as anticoagulant agents for treatment and prevention of thromboembolic disorders.

BACKGROUND OF THE INVENTION

WO 96/28427 describes benzamidine anticoagulants of the formula:

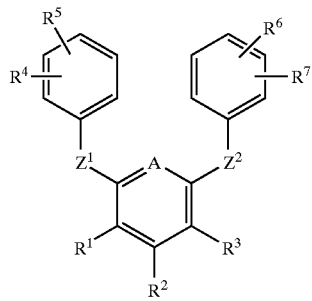

wherein $Z^1$ and $Z^2$ are O, N(R), S or $OCH_2$ and the central ring may be phenyl or a variety of heterocycles. The presently claimed compounds do not contain the $Z^1$ linker or the substitution pattern of the above compounds.

WO 95/13155 and PCT International Application U.S. 96/07692 describe isoxazoline and isoxazole fibrinogen receptor antagonists of the formula:

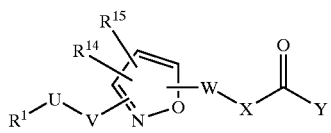

wherein $R^1$ may be a basic group, U—V may be a six-membered aromatic ring, W—X may be a variety of linear or cyclic groups, and Y is an oxy group. Thus, these compounds all contain an acid functionality (i.e., W—X—C(=O)—Y). In contrast, the presently claimed compounds do not contain such an acid functionality.

EP 0,513,387 depicts active oxygen inhibitors which are oxazoles or thiazoles of the formula:

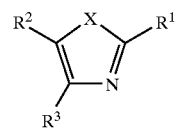

wherein X is O or S, $R^2$ is preferably hydrogen, and both $R^1$ and $R^3$ are substituted cyclic groups, with at least one being phenyl. The presently claimed invention does not relate to these types of oxazoles or thiazoles.

WO 95/18111 addresses fibrinogen receptor antagonists, containing basic and acidic termini, of the formula:

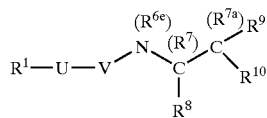

wherein $R^1$ represents the basic termini, U is an alkylene or heteroatom linker, V may be a heterocycle, and the right hand portion of the molecule represents the acidic termini. The presently claimed compounds do not contain the acidic termini of WO 95/18111.

In U.S. Pat. No. 5,463,071, Himmelsbach et al depict cell aggregation inhibitors which are 5-membered heterocycles of the formula:

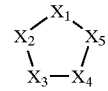

wherein the heterocycle may be aromatic and groups A-B-C- and F-E-D- are attached to the ring system. A-B-C- can be a wide variety of substituents including a basic group attached to an aromatic ring. The F-E-D- group, however, would appear to be an acidic functionality which differs from the present invention. Furthermore, use of these compounds as inhibitors of factor Xa is not discussed.

Baker et al, in U.S. Pat. No. 5,317,103, discuss 5-$HT_1$ agonists which are indole substituted five-membered heteroaromatic compounds of the formula:

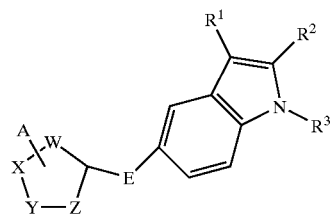

wherein $R^1$ may be pyrrolidine or piperidine and A may be a basic group including amino and amidino. Baker et al, however, do not indicate that A can be a substituted ring system like that contained in the presently claimed heteroaromatics.

Baker et al, in WO 94/02477, discuss 5-$HT_1$ agonists which are imidazoles, triazoles, or tetrazoles of the formula:

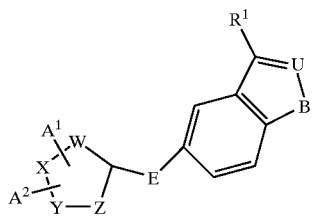

wherein $R^1$ represents a nitrogen containing ring system or a nitrogen substituted cyclobutane, and A may be a basic group including amino and amidino. But, Baker et al do not indicate that A can be a substituted ring system like that contained in the presently claimed heteroaromatics.

Tidwell et al, in *J. Med. Chem.* 1978, 21(7), 613–623, describe a series of diarylamidine derivatives including 3,5-bis(4-amidinophenyl)isoxazole. This series of compounds was tested against thrombin, trypsin, and pancreatic kallikrein. The presently claimed invention does not include these types of compounds.

Activated factor Xa, whose major practical role is the generation of thrombin by the limited proteolysis of prothrombin, holds a central position that links the intrinsic and extrinsic activation mechanisms in the final common pathway of blood coagulation. The generation of thrombin, the final serine protease in the pathway to generate a fibrin clot, from its precursor is amplified by formation of prothrombinase complex (factor Xa, factor V, $Ca^{2+}$ and phospholipid). Since it is calculated that one molecule of factor Xa can generate 138 molecules of thrombin (Elodi, S., Varadi, K.: *Optimization of conditions for the catalytic effect of the factor IXa-factor VIII Complex: Probable role of the complex in the amplification of blood coagulation. Thromb. Res.* 1979, 15, 617–629), inhibition of factor Xa may be more efficient than inactivation of thrombin in interrupting the blood coagulation system.

Therefore, efficacious and specific inhibitors of factor Xa are needed as potentially valuable therapeutic agents for the treatment of thromboembolic disorders. It is thus desirable to discover new factor Xa inhibitors.

SUMMARY OF THE INVENTION

Accordingly, the present invention provides novel guanidine mimics that are useful as factor Xa inhibitors or pharmaceutically acceptable salts or prodrugs thereof.

The present invention also provides pharmaceutical compositions comprising a pharmaceutically acceptable carrier and a therapeutically effective amount of at least one of the compounds of the present invention or a pharmaceutically acceptable salt or prodrug form thereof.

The present invention also provides a method for treating thromboembolic disorders comprising administering to a host in need of such treatment a therapeutically effective amount of at least one of the compounds of the present invention or a pharmaceutically acceptable salt or prodrug form thereof.

These and other features, which will become apparent during the following detailed description, have been achieved by the inventors' discovery that compounds of formula (I):

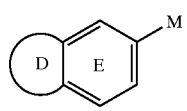

or pharmaceutically acceptable salt or prodrug forms thereof, wherein D, E, and M are defined below, are effective factor Xa inhibitors.

DETAILED DESCRIPTION OF PREFERRED EMBODIMENTS

[1] Thus, in a first embodiment, the present invention provides novel compounds of formula I:

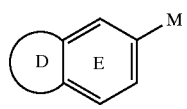

or a stereoisomer or pharmaceutically acceptable salt thereof, wherein;

ring D is selected from $-CH_2N=CH-$, $-CH_2CH_2N=CH-$, a 5–6 membered aromatic system containing from 0–2 heteroatoms selected from the group N, O, and S;

ring D is substituted with 0–2 R, provided that when ring D is unsubstituted, it contains at least one heteroatom;

ring E contains 0–2 N atom and is substituted by 0–1 R

R is selected from Cl, F, Br, I, OH, $C_{1-3}$ alkoxy, $NH_2$, $NH(C_{1-3}$ alkyl), $N(C_{1-3}$ alkyl)$_2$, $CH_2NH_2$, $CH_2NH(C_{1-3}$ alkyl), $CH_2N(C_{1-3}$ alkyl)$_2$, $CH_2CH_2NH_2$, $CH_2CH_2NH(C_{1-3}$ alkyl), and $CH_2CH_2N(C_{1-3}$ alkyl)$_2$;

M is selected from the group:

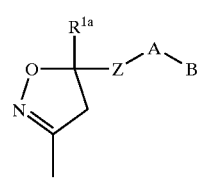

a

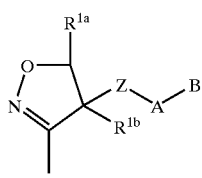

b

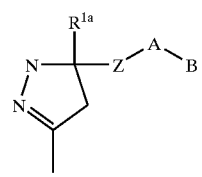

c

-continued
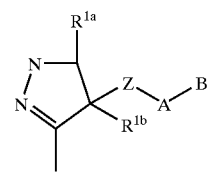
d
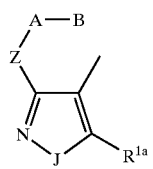
e
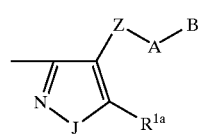
f
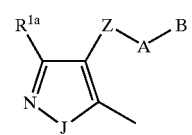
g
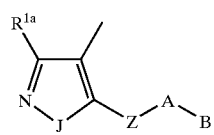
h
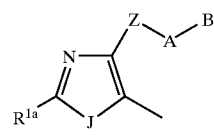
i
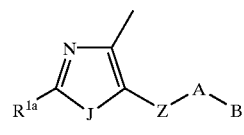
j
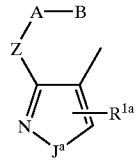
k
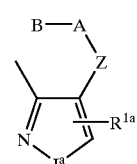
l
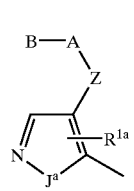
m
-continued
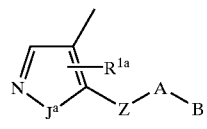
n
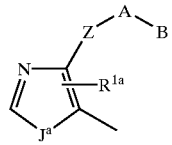
o
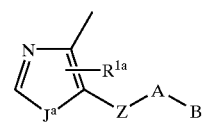
p
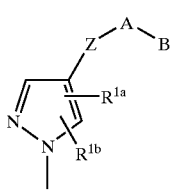
q
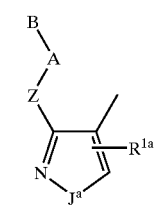
r
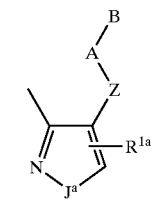
s
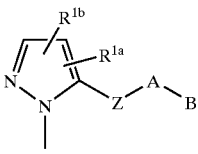
t
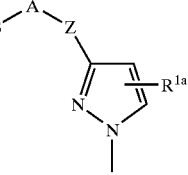
u
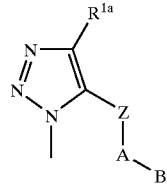
v -continued
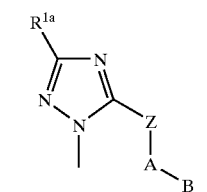  w
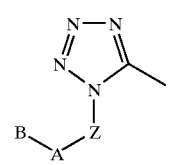  x
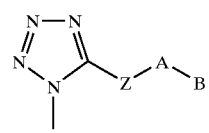  y
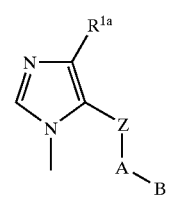  z
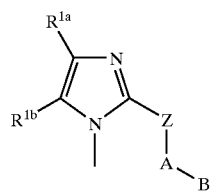  aa
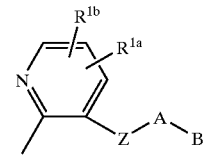  bb
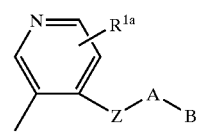  cc
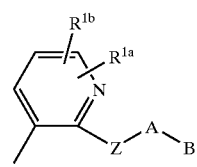  dd
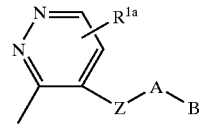  ee
-continued
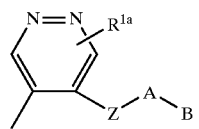  ff
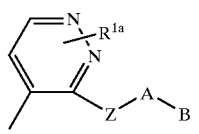  gg
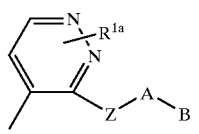  hh
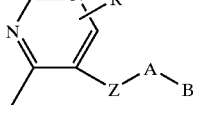  ii
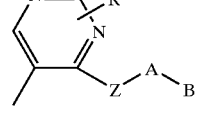  jj
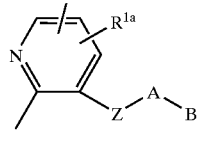  kk
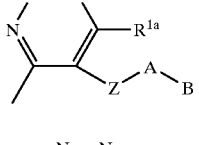  ll
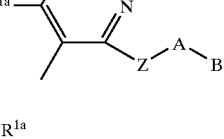  mm
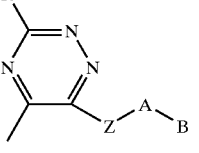  nn
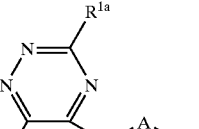  
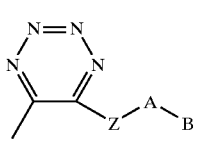  oo pp

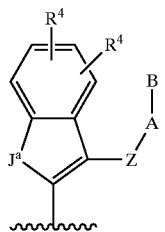

qq

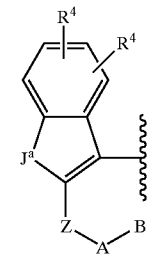

rr

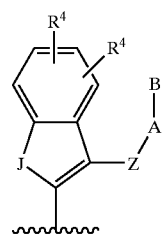

ss and

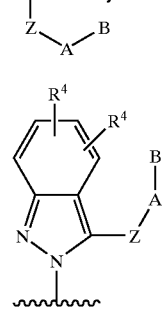

tt

J is O or S;

$J^a$ is NH or $NR^{1a}$;

Z is selected from a bond, $C_{1-4}$ alkylene, $(CH_2)_rO(CH_2)_r$, $(CH_2)_rNR^3(CH_2)_r$, $(CH_2)_rC(O)(CH_2)_r$, $(CH_2)_rC(O)O(CH_2)_r$, $(CH_2)_rOC(O)(CH_2)_r$, $(CH_2)_rC(O)NR^3(CH_2)_r$, $(CH_2)_rNR^3C(O)(CH_2)_r$, $(CH_2)_rOC(O)O(CH_2)_r$, $(CH_2)_rOC(O)NR^3(CH_2)_r$, $(CH_2)_rNR^3C(O)O(CH_2)_r$, $(CH_2)_rNR^3C(O)NR^3(CH_2)_r$, $(CH_2)_rS(O)_p(CH_2)_r$, $(CH_2)_rSO_2NR^3(CH_2)_r$, $(CH_2)_rNR^3SO_2(CH_2)_r$, and $(CH_2)_rNR^3SO_2NR^3(CH_2)_r$, provided that Z does not form a N—N, N—O, N—S, $NCH_2N$, $NCH_2O$, or $NCH_2S$ bond with ring M or group A;

$R^{1a}$ and $R^{1b}$ are independently absent or selected from $-(CH_2)_r-R^{1'}$, $-CH=CH-R^{1'}$, $NCH_2R^{1''}$, $OCH_2R^{1''}$, $SCH_2R^{1''}$, $NH(CH_2)_2(CH_2)_rR^{1'}$, $O(CH_2)_2(CH_2)_rR^{1'}$, and $S(CH_2)_2(CH_2)_rR^{1'}$;

alternatively, $R^{1a}$ and $R^{1b}$, when attached to adjacent carbon atoms, together with the atoms to which they are attached form a 5–8 membered saturated, partially saturated or unsaturated ring substituted with 0–2 $R^4$ and which contains from 0–2 heteroatoms selected from the group consisting of N, O, and S;

alternatively, when Z is C(O)NH and $R^{1a}$ is attached to a ring carbon adjacent to Z, then $R^{1a}$ is a C(O) which replaces the amide hydrogen of Z to form a cyclic imide;

$R^{1'}$ is selected from H, $C_{1-3}$ alkyl, F, Cl, Br, I, —CN, —CHO, $(CF_2)_rCF_3$, $(CH_2)_rOR^2$, $NR^2R^{2a}$, $C(O)R^{2c}$, $OC(O)R^2$, $(CF_2)_rCO_2R^{2c}$, $S(O)_pR^{2b}$, $NR^2(CH_2)_rOR^2$, $CH(=NR^{2c})NR^2R^{2a}$, $NR^2C(O)R^{2b}$, $NR^2C(O)NHR^{2b}$, $NR^2C(O)_2R^{2a}$, $OC(O)NR^{2a}R^{2b}$, $C(O)NR^2R^{2a}$, $C(O)NR^2(CH_2)_rOR^2$, $SO_2NR^2R^{2a}$, $NR^2SO_2R^{2b}$, $C_{3-6}$ carbocyclic residue substituted with 0–2 $R^4$, and 5–10 membered heterocyclic system containing from 1–4 heteroatoms selected from the group consisting of N, O, and S substituted with 0–2 $R^4$;

$R^{1''}$ is selected from H, $CH(CH_2OR^2)_2$, $C(O)R^{2c}$, $C(O)NR^2R^{2a}$, $S(O)R^{2b}$, $S(O)_2R^{2b}$, and $SO_2NR^2R^{2a}$;

$R^2$, at each occurrence, is selected from H, $CF_3$, $C_{1-6}$ alkyl, benzyl, $C_{3-6}$ carbocyclic residue substituted with 0–2 $R^{4b}$, and 5–6 membered heterocyclic system containing from 1–4 heteroatoms selected from the group consisting of N, O, and S substituted with 0–2 $R^{4b}$;

$R^{2a}$, at each occurrence, is selected from H, $CF_3$, $C_{1-6}$ alkyl, benzyl, phenethyl, $C_{3-6}$ carbocyclic residue substituted with 0–2 $R^{4b}$, and 5–6 membered heterocyclic system containing from 1–4 heteroatoms selected from the group consisting of N, O, and S substituted with 0–2 $R^{4b}$;

$R^{2b}$, at each occurrence, is selected from $CF_3$, $C_{1-4}$ alkoxy, $C_{1-6}$ alkyl, benzyl, $C_{3-6}$ carbocyclic residue substituted with 0–2 $R^{4b}$, and 5–6 membered heterocyclic system containing from 1–4 heteroatoms selected from the group consisting of N, O, and S substituted with 0–2 $R^{4b}$;

$R^{2c}$, at each occurrence, is selected from $CF_3$, OH, $C_{1-4}$ alkoxy, $C_{1-6}$ alkyl, benzyl, $C_{3-6}$ carbocyclic residue substituted with 0–2 $R^{4b}$, and 5–6 membered heterocyclic system containing from 1–4 heteroatoins selected from the group consisting of N, O, and S substituted with 0–2 $R^{4b}$;

alternatively, $R^2$ and $R^{2a}$, together with the atom to which they are attached, combine to form a 5 or 6 membered saturated, partially saturated or unsaturated ring substituted with 0–2 $R^{4b}$ and containing from 0–1 additional heteroatoms selected from the group consisting of N, O, and S;

$R^3$, at each occurrence, is selected from H, $C_{1-4}$ alkyl, and phenyl;

$R^{3a}$, at each occurrence, is selected from H, $C_{1-4}$ alkyl, and phenyl;

$R^{3b}$, at each occurrence, is selected from H, $C_{1-4}$ alkyl, and phenyl;

$R^{3c}$, at each occurrence, is selected from $C_{1-4}$ alkyl, and phenyl;

A is selected from:

$C_{3-10}$ carbocyclic residue substituted with 0–2 $R^4$, and 5–10 membered heterocyclic system containing from 1–4 heteroatoms selected from the group consisting of N, O, and S substituted with 0–2 $R^4$;

B is selected from: H, Y, and X—Y;

X is selected from $C_{1-4}$ alkylene, —$CR^2(CR^2R^{2b})(CH_2)_t$—, —C(O)—, —C(=NR$^{1"}$)—, —$CR^2(NR^{1"}R^2)$—, —$CR^2(OR^2)$—, —$CR^2(SR^2)$—, —C(O)$CR^2R^{2a}$—, —$CR^2R^{2a}$C(O), —S(O)$_p$—, —S(O)$_p$$CR^2R^{2a}$—, —$CR^2R^{2a}$S(O)$_p$—, —S(O)$_2$NR$^2$—, —NR$^2$S(O)$_2$—, —NR$^2$S(O)$_2$$CR^2R^{2a}$—, —$CR^2R^{2a}$S(O)$_2$NR$^2$—, —NR$^2$S(O)$_2$NR$^2$—, —C(O)NR$^2$—, —NR$^2$C(O)—, —C(O)NR$^2$$CR^2R^{2a}$—, —NR$^2$C(O)$CR^2R^{2a}$—, —$CR^2R^{2a}$C(O)NR$^2$—, —$CR^2R^{2a}$NR$^2$C(O)—, —NR$^2$C(O)O—, —OC(O)NR$^2$—, —NR$^2$C(O)NR$^2$—, —NR$^2$—, —NR$^2$$CR^2R^{2a}$—, —$CR^2R^{2a}$NR$^2$—, O, —$CR^2R^{2a}$O—, and —OC$R^2R^{2a}$—;

Y is selected from:
(CH$_2$)$_r$NR$^2$R$^{2a}$, provided that X—Y do not form a N—N, O—N, or S—N bond,
$C_{3-10}$ carbocyclic residue substituted with 0–2 R$^{4a}$, and
5–10 membered heterocyclic system containing from 1–4 heteroatoms selected from the group consisting of N, O, and S substituted with 0–2 R$^{4a}$;

$R^4$, at each occurrence, is selected from H, =O, (CH$_2$)$_r$OR$^2$, F, Cl, Br, I, $C_{1-4}$ alkyl, —CN, NO$_2$, (CH$_2$)$_r$NR$^2$R$^{2a}$, (CH$_2$)$_r$C(O)R$^{2c}$, NR$^2$C(O)R$^{2b}$, C(O)NR$^2$R$^{2a}$, NR$^2$C(O)NR$^2$R$^{2a}$, CH(=NR$^2$)NR$^2$R$^{2a}$, CH(=NS(O)$_2$R$^5$)NR$^2$R$^{2a}$, NHC(=NR$^2$)NR$^2$R$^{2a}$, C(O)NHC(=NR$^2$)NR$^2$R$^{2a}$, SO$_2$NR$^2$R$^{2a}$, NR$^2$SO$_2$NR$^2$R$^{2a}$, NR$^2$SO$_2$—$C_{1-4}$ alkyl, NR$^2$SO$_2$R$^5$, S(O)$_p$R$^5$, (CF$_2$)$_r$CF$_3$, NCH$_2$R$^{1"}$, OCH$_2$R$^{1"}$, SCH$_2$R$^{1"}$, N(CH$_2$)$_2$(CH$_2$)$_t$ R$^{1"}$, O(CH$_2$)$_2$(CH$_2$)$_t$R$^{1"}$, and S(CH$_2$)$_2$(CH$_2$)$_t$R$^{1"}$;

alternatively, one $R^4$ is a 5–6 membered aromatic heterocycle containing from 1–4 heteroatoms selected from the group consisting of N, O, and S;

provided that if B is H, then $R^4$ is other than tetrazole, C(O)-alkoxy, and C(O)NR$^2$R$^{2a}$;

$R^{4a}$, at each occurrence, is selected from H, =O, (CH$_2$)$_r$OR$^2$, (CH$_2$)$_r$—F, (CH$_2$)$_r$—Br, (CH$_2$)$_r$—Cl, I, $C_{1-4}$ alkyl, —CN, NO$_2$, (CH$_2$)$_r$NR$^2$R$^{2a}$, (CH$_2$)$_r$NR$^2$R$^{2b}$, (CH$_2$)$_r$C(O)R$^{2c}$, NR$^2$C(O)R$^{2b}$, C(O)NR$^2$R$^{2a}$, C(O)NH(CH$_2$)$_2$NR$^2$R$^{2a}$, NR$^2$C(O)NR$^2$R$^{2a}$, CH(=NR$^2$)NR$^2$R$^{2a}$, NHC(=NR$^2$)NR$^2$R$^{2a}$, SO$_2$NR$^2$R$^{2a}$, NR$^2$SO$_2$NR$^2$R$^{2a}$, NR$^2$SO$_2$—$C_{1-4}$ alkyl, C(O)NHSO$_2$—$C_{1-4}$ alkyl, NR$^2$SO$_2$R$^5$, S(O)$_p$R$^5$, and (CF$_2$)$_r$CF$_3$;

alternatively, one $R^{4a}$ is a 5–6 membered aromatic heterocycle containing from 1–4 heteroatoms selected from the group consisting of N, O, and S and substituted with 0–1 R$^5$;

$R^{4b}$, at each occurrence, is selected from H, =O, (CH$_2$)$_r$OR$^3$, F, Cl, Br, I, $C_{1-4}$ alkyl, —CN, NO$_2$, (CH$_2$)$_r$NR$^3$R$^{3a}$, (CH$_2$)$_r$C(O)R$^3$, (CH$_2$)$_r$C(O)OR$^{3c}$, NR$^3$C(O)R$^{3a}$, C(O)NR$^3$R$^{3a}$, NR$^3$C(O)NR$^3$R$^{3a}$, CH(=NR$^3$)NR$^3$R$^{3a}$, NH$^3$C(=NR$^3$)NR$^3$R$^{3a}$, SO$_2$NR$^3$R$^{3a}$, NR$^3$SO$_2$NR$^3$R$^{3a}$, NR$^3$SO$_2$—$C_{1-4}$ alkyl, NR$^3$SO$_2$CF$_3$, NR$^3$SO$_2$-phenyl, S(O)$_p$CF$_3$, S(O)$_p$—$C_{1-4}$ alkyl, S(O)$_p$-phenyl, and (CF$_2$)$_r$CF$_3$;

$R^5$, at each occurrence, is selected from CF$_3$, $C_{1-6}$ alkyl, phenyl substituted with 0–2 R$^6$, and benzyl substituted with 0–2 R$^6$;

$R^6$, at each occurrence, is selected from H, OH, (CH$_2$)$_r$OR$^2$, F, Cl, Br, I, $C_{1-4}$ alkyl, CN, NO$_2$, (CH$_2$)$_r$NR$^2$R$^{2a}$, (CH$_2$)$_r$C(O)R$^{2b}$, NR$^2$C(O)R$^{2b}$, NR$^2$C(O)NR$^2$R$^{2a}$, CH(=NH)NH$_2$, NHC(=NH)NH$_2$, SO$_2$NR$^2$R$^{2a}$, NR$^2$SO$_2$NR$^2$R$^{2a}$, and NR$^2$SO$_2$$C_{1-4}$ alkyl;

n is selected from 0, 1, 2, and 3;

m is selected from 0, 1, and 2;

p is selected from 0, 1, and 2;

r is selected from 0, 1, 2, and 3;

s is selected from 0, 1, and 2; and, t is selected from 0 and 1.

In a second embodiment, the present invention provides novel pharmaceutical compositions, comprising: a pharmaceutically acceptable carrier and a therapeutically effective amount of a compound of formula (I) or a pharmaceutically acceptable salt form thereof.

In a third embodiment, the present invention provides a novel method for treating or preventing a thromboembolic disorder, comprising: administering to a patient in need thereof a therapeutically effective amount of a compound of formula (I) or a pharmaceutically acceptable salt form thereof.

DEFINITIONS

The compounds herein described may have asymmetric centers. Compounds of the present invention containing an asymmetrically substituted atom may be isolated in optically active or racemic forms. It is well known in the art how to prepare optically active forms, such as by resolution of racemic forms or by synthesis from optically active starting materials. Many geometric isomers of olefins, C=N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms. All chiral, diastereomeric, racemic forms and all geometric isomeric forms of a structure are intended, unless the specific stereochemistry or isomeric form is specifically indicated.

The term "substituted," as used herein, means that any one or more hydrogens on the designated atom is replaced with a selection from the indicated group, provided that the designated atom's normal valency is not exceeded, and that the substitution results in a stable compound. When a substitent is keto (i.e., =O), then 2 hydrogens on the atom are replaced. Keto substituents are not present on aromatic moieties.

The present invention is intended to include all isotopes of atoms occurring in the present compounds. Isotopes include those atoms having the same atomic number but different mass numbers. By way of general example and without limitation, isotopes of hydrogen include tritium and deuterium. Isotopes of carbon include C-13 and C-14.

When any variable (e.g., R$^6$) occurs more than one time in any constituent or formula for a compound, its definition at each occurrence is independent of its definition at every other occurrence. Thus, for example, if a group is shown to be substituted with 0–2 R$^6$, then said group may optionally be substituted with up to two R$^6$ groups and R$^6$ at each occurrence is selected independently from the definition of R$^6$. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent. Combinations of substituents and/or variables are permissible only if such combinations result in stable compounds.

As used herein, "$C_{1-6}$ alkyl" is intended to include both branched and straight-chain saturated aliphatic hydrocarbon groups having the specified number of carbon atoms, examples of which include, but are not limited to, methyl, ethyl, n-propyl, i-propyl, n-butyl, i-butyl, sec-butyl, t-butyl, pentyl, and hexyl; "Alkenyl" is intended to include hydrocarbon chains of either a straight or branched configuration and one or more unsaturated carbon-carbon bonds which may occur in any stable point along the chain, such as ethenyl, propenyl, and the like.

"Halo" or "halogen" as used herein refers to fluoro, chloro, bromo, and iodo; and "counterion" is used to represent a small, negatively charged species such as chloride, bromide, hydroxide, acetate, sulfate, and the like.

As used herein, "carbocycle" or "carbocyclic residue" is intended to mean any stable 3- to 7-membered monocyclic or bicyclic or 7- to 13-membered bicyclic or tricyclic, any of which may be saturated, partially unsaturated, or aromatic. Examples of such carbocycles include, but are not limited to, cyclopropyl, cyclobutyl, cyclopentyl, cyclohexyl, cycloheptyl, adamantyl, cyclooctyl,; [3.3.0]bicyclooctane, [4.3.0]bicyclononane, [4.4.0]bicyclodecane (decalin), [2.2.2]bicyclooctane, fluorenyl, phenyl, naphthyl, indanyl, adamantyl, or tetrahydronaphthyl (tetralin).

As used herein, the term "heterocycle" or "heterocyclic system" is intended to mean a stable 5- to 7-membered monocyclic or bicyclic or 7- to 10-membered bicyclic heterocyclic ring which is saturated partially unsaturated or unsaturated (aromatic), and which consists of carbon atoms and from 1 to 4 heteroatoms independently selected from the group consisting of N, O and S and including any bicyclic group in which any of the above-defined heterocyclic rings is fused to a benzene ring. The nitrogen and sulfur heteroatoms may optionally be oxidized. The heterocyclic ring may be attached to its pendant group at any heteroatom or carbon atom which results in a stable structure. The heterocyclic rings described herein may be substituted on carbon or on a nitrogen atom if the resulting compound is stable. If specifically noted, a nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1. As used herein, the term "aromatic heterocyclic system" is intended to mean a stable 5- to 7-membered monocyclic or bicyclic or 7- to 10-membered bicyclic heterocyclic aromatic ring which consists of carbon atoms and from 1 to 4 heterotams independently selected from the group consisting of N, O and S. It is preferred that the total number of S and O atoms in the aromatic heterocycle is not more than 1.

Examples of heterocycles include, but are not limited to, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazalinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isobenzofuranyl, isochromanyl, isoindazolyl, isoindolinyl, isoindolyl, isoquinolinyl, isothiazolyl, isoxazolyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl. Preferred heterocycles include, but are not limited to, pyridinyl, furanyl, thienyl, pyrrolyl, pyrazolyl, pyrrolidinyl, imidazolyl, indolyl, benzimidazolyl, 1H-indazolyl, oxazolidinyl, benzotriazolyl, benzisoxazolyl, oxindolyl, benzoxazolinyl, or isatinoyl. Also included are fused ring and spiro compounds containing, for example, the above heterocycles.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences*, 17th ed., Mack Publishing Company, Easton, Pa., 1985, p. 1418, the disclosure of which is hereby incorporated by reference.

"Prodrugs" are intended to include any covalently bonded carriers which release the active parent drug according to formula (I) in vivo when such prodrug is administered to a mammalian subject. Prodrugs of a compound of formula (I) are prepared by modifying functional groups present in the compound in such a way that the modifications are cleaved, either in routine manipulation or in vivo, to the parent compound. Prodrugs include compounds of formula (I) wherein a hydroxy, amino, or sulfhydryl group is bonded to any group that, when the prodrug or compound of formula (I) is administered to a mammalian subject, cleaves to form a free hydroxyl, free amino, or free sulfhydryl group, respectively. Examples of prodrugs include, but are not limited to, acetate, formate and benzoate derivatives of alcohol and amine functional groups in the compounds of formula (I), and the like.

"Stable compound" and "stable structure" are meant to indicate a compound that is sufficiently robust to survive isolation to a useful degree of purity from a reaction mixture, and formulation into an efficacious therapeutic agent.

Other features of the invention will become apparent in the course of the following descriptions of exemplary embodiments that are given for illustration of the invention and are not intended to be limiting thereof.

EXAMPLES

Example 1

1-(1'-Amino-isoquinol-7'-yl)-3-methyl-5-[(2'-aminosulfonyl-[1,1']-biphen-4-yl)carbonylamino] pyrazole, mesylate salt 7-Aminoisoquinoline (6.26 g, 43.4 mmol) (*J. Chem. Soc.* 1951, 2851) is added to 40 mL of concentrated hydrochloric acid at 0° C. Sodium nitrite (3.0 g, 43.4 mmol) is dissolved in 15 mL water, cooled to 0° C., and added dropwise to the isoquinoline solution. The reaction is stirred for 30 min at 0° C. Stannous chloride dihydrate (29.3 g, 130.2 mmol, 3 eq) is dissolved in 25 mL concentrated hydrochloric acid, the solution cooled to 0° C., and added dropwise to the isoquinoline solution. The reaction is placed in the refrigerator overnight. The next day the precipitate is isolated by filtration, washed with 100 mL ice cold brine followed by 100 mL of a 2:1 petroleum ether/ethyl ether solution. The brown solid is dried under dynamic vacuum overnight. The tin double salt of the isoquinoline (9.0 g, 26 mmol) is suspended in 100 mL glacial acetic acid and ethyl 2,4-dioxopentanoate oxime (4.0 g, 21.3 mmol) added dropwise. The reaction was brought to reflux overnight. The next day the acetic acid was evaporated and to the residue was added 100 mL water, cooled to 0° C. and neutralized with solid sodium bicarbonate. The solution was extracted with ethyl acetate (6×50 mL), dried over sodium sulfate, and evaporated to give the title compound as a brownish solid (5.15 g, 86% yield) which was >85% of the desired pyazole regioisomer. The material may be purified by silica gel flash chromatography eluting with 5% methanol in chloroform: $^1$H NMR (CDCl$_3$) δ 1.24 (t, 3H, J=7.1 Hz, OCH$_2$CH$_3$), 2.40 (s, 3H, pyrazole CH$_3$), 4.24 (q, 2H, J=7.1 Hz, OCH$_2$CH$_3$), 6.89 (s, 1H, pyrazole H), 7.70 (d, 1H, J=5.9 Hz, H4), 7.75 (dd, 1H, J=8.8 Hz, J=2.2 Hz, H6), 7.89 (d, 1H, J=8.8 Hz, H5), 8.05 (d, 1H, J=2.0 Hz, H7), 8.58 (s, 1H, J=5.9 Hz, H3), 9.29 (s, 1H, H1), MS (ES+): 282.1 (M+H)$^+$ (100%), C$_{30}$H$_{29}$N$_5$O$_3$S 539.65.

To a solution of 2'-tert-butylaminosulfonyl-[1,1']-biphenyl-4-ylamine (2.19 g, 7.19 mmol) in 100 mL of anhydrous dichloromethane under an atmosphere of nitrogen was added dropwise trimethyl aluminium (10.9 mL, 21.6 mmol, 2M in hexane). The solution was stirred for 30 min at ambient temperature. Ethyl 1-(isoquinolyn-7'-yl)-3-methyl-5-pyrazole carboxylate (2.02 g, 7.19 mmol) in 70 mL of anhydrous dichloromethane was added dropwise and the reaction warmed to 40° C. and allowed to stir for 15 hours. The reaction was quenched with 50 mL 1N hydrochloric acid at 0° C., diluted with 50 mL water and made basic with solid sodium carbonate. The phases are separated and the aqueous extracted with dichloromethane (3×30 mL), dried over sodium sulfate, and evaporated to give the amide (3.50 g, 90% yield) as a brown solid and of sufficient purity for the next step. The material may be purified by silica gel flash chromatography eluting with 5% methanol in chloroform. MS (ES+): 540.22 (M+H)$^+$ (100%). The amide was dissolved in 60 mL acetone to which was added meta-chloroperbenzoic acid (70%) (1.86 g, 7.55 mmol) and the reaction allowed to stir overnight at ambient temperature. The next day the solvent was removed under reduced pressure and the residue taken up in 100 mL each of ethyl acetate and saturated sodium bicarbonate. The phases are separated and the organic dried over sodium sulfate, and evaporated to give the N-oxide as a pale red solid in quantitative yield and of sufficient purity for the next step. MS (ES+): 556.20 (M+H)$^+$ (15%); 578.21 (M+Na)$^+$ (100%).

The N-oxide was dissolved in 110 mL of anhydrous pyridine and tosyl chloride (1.64 g, 8.63 mmol) was added in three equal portions and the reaction allowed to stir at ambient temperature overnight. The pyridine was removed under reduced pressure and to the residue was added 45 mL ethanolamine and the reaction stirred at ambient temperature for 2 days. The reaction was poured onto cracked ice and the solids isolated by filtration and dried under vacuum to yield 2.33 g (65% yield) of a mixture of 1-aminoisoquinoline (major) and 4-aminoisoquinoline (minor) products as a tan solid. MS (ES+) 555.22 (M+H)$^+$ (100%), HRMS (FAB+) for C$_{30}$H$_{30}$N$_6$O$_3$S calc. (M+H)$^+$ 555.217836; found 555.21858.

To 20 mL of trifluoroactic acid was added the 1-aminoisoquinoline compound and the reaction brought to reflux overnight. The next day the solvent was removed under reduced pressure and the residue made basic with aqueous sodium carbonate cooled to 0° C., extracted with ethyl acetate (3×40 mL), dried over sodium sulfate, and evaporated. The tan solid was purified by silica gel flash column chromatography eluting with 15% MeOH/CHCl$_3$ to give 1.60 g (76% yield) of the title compound as a light tan solid. MS (ES+) 499.14 (M+H)$^+$ (100%), HRMS (FAB+) for C$_{26}$H$_{22}$N$_6$O$_3$S calc. (M+H)$^+$ 499.155236; found 499.153551.

The product was then treated with one equivalent of methane sulfonic acid in THF. Evaporation of the solvent gave Example 1, MS (ES+) 499.0 (M+H)$^+$ (100%), mp 195° C.

Example 2

1-(1'-Amino-isoquinol-7'-yl)-3-methyl-5-[(2'-methylsulfonyl-[1,1']-biphen-4-yl)carbonylamino] pyrazole mesylate The title compound was prepared analogously to Example 1. MS (ES+) 498.0 (M+H)$^+$ (100%), mp 175° C.

Example 3

1-(4'-Amino-isoquinol-7'-yl)-3-methyl-5-[(2'-aminosulfonyl-[1,1']-biphen-4-yl)carbonylamino] pyrazole The title compound was prepared analogously to Example 1. MS (ES+) 499.0 (M+H)$^+$ (100%), mp 204° C.

Example 4

1-(Isoquinol-7'-yl)-3-methyl-5-[(2'-aminosulfonyl-[1,1']-biphen-4-yl)carbonylamino]pyrazole The title compound was prepared analogously to Example 1. MS (ES+) 484.1 (M+H)+ (100%).

Example 5

3-(1'-Amino-isoquinol-7'-yl)-5-[(2'-aminosulfonyl-[1,1']-biphen-4-yl)carbonylamino]-5-methylisoxazoline The title compound was prepared analogously to Example 1. MS (ES+) 502.3 (M+H)+ (100%).

Example 6

3-(Isoquinol-5'-yl)-5-[(2'-aminosulfonyl-[1,1']-biphen-4-yl)carbonylamino]-5-methylisoxazoline The title compound was prepared analogously to Example 1. MS (ES+) 487.3 (M+H)+ (100%).

Example 7

3-(Isoquinol-7'-yl)-5-[(2'-aminosulfonyl-[1,1']-biphen-4-yl)carbonylamino]-5-methylisoxazoline The title compound was prepared analogously to Example 1. MS (ES+) 487.3 (M+H)+ (100%).

Example 8

3-(2'-Aminobenzimidazol-5'-yl)-5-[(2'-aminosulfonyl-[1,1']-biphen-4-yl)aminocarbonyl]-5-methylisoxazoline To a solution of methyl 3,4-diaminobenzoate (7.50 g) in methanol (225 mL) was added N,N'-dicarbobenzyloxy methyl isothiourea (16.20 g). The reaction mixture was brought to reflux for 4 h. Heat was removed and the mixture was allowed to cool. The stirring was continued at rt for overnight. The precipitate was filtered and washed with ether (40 mL) and air dried to give 2-benzyloxycarbonylamino-5-methoxycarbonylbenzimidazole (9.80 g) as a purple solid. ESI mass spectrum z (rel. intensity) 326 (M+H. 100).

A suspension of benzimidazole (1.58 g) in methylene chloride (40 mL) was cooled to −78° C. DIBAL (1.0 M in $CH_2Cl_2$, 21.87 mL) was added via syringe. The reaction mixture was stirred at −78° C. for 1.5 h. and slowly warmed up to rt. The reaction was quenched with methanol (2 mL), HCl (5%, 2 mL). The solvent was removed and the residue partitioned between ethyl acetate (60 mL) and water (60 mL), washed with water (2×40 mL), brine (40 mL); dried over sodium sulfate, to give 2-benzyloxycarbonylamino-5-hydroxymethylbenzimidazole (1.2 g). ESI mass spectrum z(rel. intensity) 298 (M+H, 100).

To a solution of pyridine (3.83 g) in methylene chloride (30 mL) was added $CrO_3$ (2.42 g). The mixture was stirred at rt for 45 minutes followed by addition of a solution of 2-benzyloxycarbonylamino-5-hydroxymethylbenzimidazole (1.2 g) in methylene chloride (20 mL) and DMF (10 mL). The reaction mixture was stirred at rt for 2.5 h. Two thirds of the solvent was removed and the residue was partitioned between ethyl acetate and sodium bicarbonate (sat.), washed with $KHSO_4$ (5% in $H_2O$), water and brine; dried over sodium sulfate to give aldehyde (0.95 g). ESI mass spectrum z (rel. intensity) 296 (M+H, 100).

To a solution of aldehyde (0.50 g) in ethanol was added a solution of hydroxyamine hydrochloride (0.15 g) in water (5 mL) and a solution of sodium acetate (0.28 g) in water (5 mL). The reaction mixture was stirred at rt overnight. Next day, ethanol was removed and the white precipitate was filtered, washed with water and air dried to give the oxime (0.50 g). ESI mass spectrum z (rel. intensity) 311 (M+H, 100).

To a solution of 2-benzyloxycarbonylamino-5-oximebenzimidazole (0.31 g) in THF (50 mL) was added methyl acrylic acid (0.11 g), to this mixture was added bleach (5.25%, 2.4 mL) dropwise at 0° C. under stirring. After addition of bleach, the stirring was continued at rt overnight. Most of the solvent was removed and the mixture was partitioned between ethyl acetate and water. The organic was separated and washed with water, brine; dried over sodium sulfate. The resulting solid was recrystallized using methylene chloride/hexane (1:1) to give isoxazoline (0.25 g) as a pure compound. ESI mass spectrum z (rel. intensity) 395 (M+H, 100).

To a solution of isoxazoline (100 mg) in DMF (5 mL) was added triethylamine (39 mg), (2'-tert-butylaminosulfonyl-[1,1']-biphenyl-4-yl)amine (115 mg) and BOP (168 mg). The reaction mixture was stirred at 55° C. overnight. Next day, the mixture was partitioned between ethylacetate (25 mL) and water (25 mL), washed with HCl (5%, 4×10 mL), sodium bicarbonate (5%, 2×10 mL), water (2×10 mL) and brine (10 mL); dried over sodium sulfate, filtered and concentrated to leave 3-(2-benzyloxycarbonylamino-5-yl)-5-[(2'-tert-butylaminosulfonyl-[1,1']-biphenyl-4-yl) aminocarbonyl]-5-methylisoxazoline (120 mg). ESI mass spectrum z (rel. intensity) 681 (M+H, 100).

3-(2-Benzyloxycarbonylamino-5-yl)-5-[(2'-tert.butylaminosulfonyl-[1,1']-biphen-4-yl)aminocarbonyl]-5-methylisoxazoline (100 mg) was dissolved in TFA (4 mL). The resulting solution was brought to reflux for 3 h., cooled to room temperature, stripped off TFA, partitioned between ethylacetate and sodium bicarbonate (5%), washed with water, dried over sodium sulfate, filtered and concentrated. Prep. TLC gave pure title compound (35 mg). ESI mass spectrum z (rel. intensity) 491 (M+H, 100), mp 162° C.

Example 9

3-(3'-Aminoindazol-5'-yl)-5-[(2'-aminosulfonyl-[1,1']-biphen-4-yl)aminocarbonyl]-5-methylisoxazoline To a solution of 2-fluoro-5-methylbenzonitrile (13.50 g) in $CCl_4$ (500 mL) was added NBS (35.60 g) and benzoylperoxide (2.40 g). The reaction mixture was brought to reflux for 16 h. Heat was removed and allow it to cool. The mixture was filtered through silic gel, filtrate was concentrated to give a 5:1 mixture (25 g) of 2-fluoro-5-bis-bromomethylbenzonitrile and 2-fluoro-5-bromomethylbenzonitrile.

The mixture (25 g) was dissolved in formic acid (85% in water, 200 mL). The resulting solution was refluxed for 4.5 h. After allowing the reaction mixture to cool to room temperature, most of the formic acid was stripped off, sodium bicarbonate was added to quench the remaining acid, it was partitioned between ethylacetate and sodium bicarbonate (sat.), washed with water and brine, dried over sodium sulfate, filtered and concentrated, flash chromatography (10% EtOAc in hexane) to give 3-cyano-4-fluorobenzaldehyde (12 g) as a white crystal. $^1$H NMR ($CDCL_3$) δ 10.0 (s, 1H), 8.15–8.24 (m, 2H), 7.42 (t, 1H) ppm; CI mass spectrum z (rel. intensity) 150 (M+H, 100).

To a solution of 3-cyano-4-fluorobenzaldehyde (1.49 g) in benzene was added 1,3-propanediol (0.91 g) and toluenesulfonic acid (0.20 g). The mixture was brought to reflux for 3 hr. with a water trap. After cooling, it was partitioned between ethylacetate and water, washed with sodium bicarbonate (15% in water), water, brine and water; dried over sodium sulfate, filtered and concentrated to give ketal (1.80 g); $^1$H NMR (CDCL3) δ 7.69–7.80 (m, 2H), 7.20 (t, 1H), 5.48 (s, 1H), 4.24–4.30 (m, 2H), 3.95–4.04 (m, 2H), 2.12–2.28 (m, 1H), 1.45–1.52 (m, 1H) ppm; CI mass spectrum z (rel. intensity) 207 (M+H, 100).

To a solution of ketal (0.6 g) in n-butanol (10 mL) was added hydrazine monohydrate (1.45 g). The reaction mixture was brought to reflux for 3 hr, cooled to room temperature, quenched with pH 5 buffer solution, partitioned between methylene chloride and water. The organic phase was separated and washed with $NH_4Cl$ (sat.), 3×$H_2O$, dried over sodium sulfate, filtered and concentrated to give ketal (0.45 g). CI mass spectrum z (rel. intensity) 220 (M+H, 100).

To a solution of ketal (0.42 g) in methylene chloride was added TEA (1.6 mL) and di-tert-butyl-dicarbonate (2.4 g). The mixture was stirred at room temperature overnight. The mixture was partitioned between methylene chloride and water, washed with pH 5 buffer solution, water and brine; dried over sodium sulfate and concentrated to give 1-tert-butoxycarbonyl-3-tert-butoxyaminoindazole-5-aldehydedioxane (0.55 g). CI mass spectrum z (rel. intensity) 420 (M+H, 100).

To a solution of indazole (0.55 g) in acetone (10 mL) was added toluene sulfonic acid (100 mg). The reaction mixture was stirred at rt for 2 h. Acetone was removed and the residue was partitioned between ethyl acetate and water, washed with 2×$H_2O$, brine and dried over sodium sulfate. Flash chromatography gave 1-tert-butoxycarbonyl-3-tert-butoxycarbonylamino-5-hydrogencarbonylindazole (0.3 g). CI mass spectrum z (rel. intensity) 362 (M+H, 100).

To a solution of indazole (0.30 g) in ethanol (6 mL) was added a solution of hydroxyamine hydrochloride (0.07 g) in water (1 mL) and another solution of sodium acetate (0.14 g) in water (1 mL). The mixture was stirred at rt overnight. Ethanol was removed and the resulting solid was filtered, washed with water and air dried to give aldoxime.

To a solution of aldoxime (0.22 g) in THF was added 2-methyacrylic acid (0.06 g) followed by dropwise addition of bleach (1.4 mL) at 0° C. with vigorous stirring. After the addition, reaction mixture was slowly warmed to rt and stirred at rt overnight. Partitioned between ethylacetate and HCl (5%), washed with 3×$H_2O$, dried over sodium sulfate, filtered and concentrated, flash chromatography to give isoxazoline (0.14 g).

To a solution of isoxazoline (0.14 g) in DMF (6 mL) was added 2'-tert-butylaminosulfonyl-[1,1']-biphenyl-4-ylamine (0.14 mg), TEA (0.05 g) and BOP reagent (0.2 g). The mixture was stirred at 50° C. overnight; partitioned between ethylacetate and water, washed with brine, 4× water, dried over sodium sulfate, filtered, concentrated and flash chromatographed to give an isoxazoline (0.06 g). ESI mass spectrum z (rel. intensity) 747 (M+H, 100).

The isoxazoline (0.06 g) was dissolved in TFA (5 mL). The resulting solution was brought to reflux for 1.5 h. The mixture was stripped off TFA, partitioned between ethylacetate and sodium bicarbonate (5%), washed with 2× water, dried over sodium sulfate, filtered and concentrated. Prep. TLC afforded example 9 (5 mg). ESI mass spectrum z (rel. intensity) 491 (M+H, 100), mp 157–159° C.

Example 10

3-(3'-Aminobenzisoxazol-5'-yl)-5-[(2'-aminosulfonyl-[1,1']-biphen-4-yl)aminocarbonyl]-5-methylisoxazoline To a solution of 3-cyano-4-fluorobenzaldehyde (2.50 g) in ethanol (40 mL) was added a solution of hydroxyamine (1.46 g) in water (10 mL), a solution of sodium acetate (2.75 g) in water (10 mL). The mixture was stirred at rt, overnight. Ethanol was removed and the white precipitate was filtered, washed with water and air dried to leave 3-cyano-4-fluorobenzaldehydeoxime (2.05 g). CI mass spectrum z (rel. intensity) 165 (M+H, 100).

To a solution of 3-cyano-4-fluorobenzaldoxime (2.50 g) in THF (100 mL) was added 2-methylacrylic acid (1.64 g). The mixture was cooled to 0° C. on an ice bath followed by dropwise addition of NaOCl (5.25% in water) (37 mL) with vigouros stirring. After the addition, the reaction mixture was slowly warmed up to rt and stirred at rt overnight. The mixture was partitioned between ethylacetate and HCl (5% in water), washed with brine, 2×$H_2O$, dried over sodium sulfate, filtered and concentrated. The resulting solid was recrystalized to give 3-(4-fluoro-3-cyanophenyl-1-yl)-5-methyl-5-hydroxycarbonylisoxazoline (3.30 g) as a pure compound. $^1$H NMR (DMSO-$d_6$) δ 13.6 (br, 1H), 8.20 (dd, 1H), 8.10 (td, 1H), 3.84 (d, 1H), 3.41 (d, 1H), 1.57 (s, 3H) ppm; ESI mass spectrum z (rel. intensity) 247 (M−H, 100).

To a solution of acetone oxime (2.60 g) in DMF (10 mL) was added potassium tert-butoxide (1.0 M in THF, 2.6 mL) via syringe. The mixture was stirred at rt 10 minutes, a solution of 3-(4-fluoro-3-cyanophen-1-yl)-5-methyl-5-hydroxycarbonylisoxazoline (0.5 g) in DMF (5 mL) was added. The reaction mixture was stirred at rt overnight. HCl (5% in water) was added to quench the reaction solution, partitioned between ethylacetate and water, washed with 2×$H_2O$, brine, 2×$H_2O$, dried over sodium sulfate, filtered and concentrated to leave isoxazoline (0.51 g) as white crystals. $^1$H NMR (CDCl$_3$) δ 9.09 (br, 1H), 7.86 (dd, 1H), 7.78 (d, 1H), 7.59 (d, 1H), 3.87 (d, 1H), 3.27 (d, 1H), 2.19 (s, 3H), 2.05 (s, 3H), 1.78 (s, 3H) ppm. CI mass spectrum z (rel. intensity) 302 (M+H, 100).

To a solution of isoxazoline (0.51 g) in ethanol (10 mL) was added HCl (20% in water, 3 mL). The mixture was brought to reflux for 1.5 h. Ethanol was removed and the residue was partitioned between ethyl acetate and water, washed with 2× water, dried over sodium sulfate, filtered and concentrated to 3-(3-aminobenzisoxazol-5-yl)-5-methyl-5-ethoxycarbonylisoxazoline (0.42 g) as white solid. $^1$H NMR (CDCl$_3$) δ 7.90 (s, 1H), 7.79 (d, 1H), 7.35, (d, 1H), 4.25 (q, 2H), 3.95 (d, 1H), 3.49 (s, 2H), 3.25 (d, 1H), 1.73, (s, 3H), 1.30 (s, 3H). CI mass spectrum z (rel. intensity) 290 (M+H, 100).

To a solution of isoxazoline (0.42 g) in THF (10 mL) was added NaOH (10% in water) (10 mL). The mixture was stirred at 60° C. for 1.5 h, cooled to rt and HCl (10% in water) was added dropwise untill pH 4–5. The mixture was partitioned between ethylacetate and water, washed with 2×$H_2O$, dried over sodium sulfate, filtered and concentrated to give isoxazoline acid (0.32 g) as a pure compound. $^1$H NMR (DMSO-$d_6$) δ 13.25 (br, 1H), 8.20 (s, 1H), 7.83 (d, 1H), 7.58 (d, 1H), 6.58 (s, 2H), 3.82 (d, 1H), 3.00 (d, 1H), 1.60 (s, 3H) ppm. ESI mass spectrum z (rel. intensity) 262 (M+H, 100).

To a solution of isoxazoline acid (52 mg) in DMF (2 mL) was added TEA (26 mg), 2'-tert-butylaminosulfonyl-[1,1']-biphenyl-4-ylamine (79 mg) and BOP reagent (115 mg). The reaction mixture was stirred at 50° C. overnight. Partitioned between ethylacetate and water, washed with 2×H$_2$O brine and 2×H$_2$O, dried over sodium sulfate, filtered and flash chromatographed to elute amide (45 mg). ESI mass spectrum z (rel. intensity) 547 (M+H, 100); mp 144° C.

The amide (40 mg) was dissolved in TFA (2 mL). The resulting solution was brought to reflux for 1.5 h., stripped off TFA and flash chromatographed to give the title compound (22 mg) as a pure compound. ESI mass spectrum z (rel. intensity) 492 (M+H, 100), mp 164° C.

Example 11

1-(3'-Aminobenzisoxazol-5'-yl)-3-methyl-5-[(2'-aminosulfonyl-[1,1']-biphen-4-yl)aminocarbonyl] pyrazole To a solution of 2-fluoro-5-nitrobenzonitrile (2.0 g) in ethylacetate (50 mL) was added stannous chloride dihydrate (27.0 g). The mixture was brought to reflux for 1.5 h and allowed to cool. The mixture was partitioned between ethyl acetate and sodium bicarbonate (sat. in water). The aqueous phase was extracted with ethyl acetate four times. The organic phase was washed with 4×H$_2$O, dried over sodium sulfate, filtered and concentrated to leave 4-fluoro-3-cyanoaniline (1.40 g). CI mass spectrum z (rel. intensity) 137 (M+H, 100).

4-Fluoro-3-cyanoaniline (1.4 g) was added to 10 mL of concentrated hydrochloric acid at 0° C. Sodium nitrite (0.71 g) was dissolved in water (3 mL), cooled to 0° C., and added dropwise to the 4-fluoro-3-cyanoaniline solution. The reaction was stirred at 0° C. for 30 minutes. Stannous chloride dihydrate (6.95 g) was dissolved in HCl (conc., 4 mL). The solution was cooled to 0° C., and added dropwise to the 4-fluoro-3-cyanoaniline solution. The reaction was placed in the refrigerator overnight. Next day, the precipitate was isolated by filtration, washed with ice cold brine (30 mL), followed by a 2:1 petrolium ether/ethylether (30 mL) solution. The yellow solid was dried under vacuum overnight to leave 4-fluoro-3-cyanophenylhyrazine tin chloride (2.5 g).

To a suspension of 4-fluoro-3-cyanophenylhyrazine tin chloride (0.9 g) in acetic acid (15 mL) was added the oxime (0.5 g). The reaction was brought to reflux overnight. The next day the acetic acid was evaporated and the residue was partitioned between ethylacetate and sodium bicarbonate (sat.). The equeous was extracted by ethylacetate (4×20 mL). The organic phase was washed with water, brine, dried over sodium sulfate, filtered and concentrated. Flash chromatography gave ethyl 1-(4-fluoro-3-cyanophenyl)-3-methyl-5-pyrazole carboxylate (0.7 g) as pure compound. CI mass spectrum z (rel. intensity) 274 (M+H, 100).

To a solution of acetone oxime (70 mg) in DMF (6 mL) was added potassium tert-butoxide (1.0M in THF, 1.1 mL). The reaction was stirred at rt for 15 minutes. A solution of ethyl 1-(4-fluoro-3-cyanophenyl)-3-methyl-5-pyrazole carboxylate (0.2 g) in DMF (3 mL) was added to the oxime solution. The reaction was stirred at rt overnight. The next day the reaction was partitioned between ethylacetate and amonium chloride (sat. in water), washed with brine, 4×H$_2$O, dried over sodium sulfate, filtered and concentrated. Flash chromatography gave 1-(4-isopropylideneaminooxy-3-cyanophenyl)-3-methyl-5-pyrazole carboxylate (0.18 g). CI mass z (rel. intensity) 327 (M+H, 100).

To a solution of 1-(4-isopropylideneaminooxy-3-cyanophenyl)-3-methyl-5-pyrazole carboxylate (0.18 g) in ethanol (5 mL) was added HCl (20%, 3 mL). The reaction was brought to reflux for 2.5 h, ethanol was evaporated and the residue was partitioned between ethylacetate and water, washed with 2×H$_2$O, dried over sodium sulfate, filtered and concentrated to give 1-(3-aminobenzisoxazole-5-yl)-3-methyl-5-pyrazole carboxylate (0.14 g). CI mass spectrum z (rel. intensity) 287 (M+H, 100).

To a solution of ethyl 1-(3-aminobenzisoxazole-5-yl)-3-methyl-5-pyrazole carboxylate (0.14 g) in THF (5 mL) was added NaOH (10% in water, 5 mL). The reaction was stirred at 60° C. for 2 h, THF was evaporated, HCl (10% in water) was added dropwisely until the pH was between 4–5, partitioned between ethylacetate and water, washed with brine, dried over sodium sulfate, filtered and concentrated to give 1-(3-aminobenzisoxazole-5-yl)-3-methyl-5-pyrazole carboxylic acid (0.11 g). ESI mass spectrum z (rel. intensity) 259 (M+H, 100).

To a solution of the pyrazole carboxylic acid (55 mg) in DMF (5 mL) was added TEA (33 mg), 2'-tert-butylaminosulfonyl-[1,1']-biphenyl-4ylamine (97 mg) and BOP reagent (141 mg). The reaction was stirred at 50° C. overnight. The next day the reaction was partitioned between ethylacetate and water, washed with brine, 4×H$_2$O, dried over sodium sulfate, filtered, concentrated and flash chromatography to give amide (85 mg). ESI mass spectrum z (rel. intensity) 567 (M+Na, 100).

The amide was dissolved in TFA (3 mL). The resulting solution was brought to reflux for 1 h. TFA was evaporated, flash chromatographed to give the title compound (60 mg) as a white solid. ESI mass spectrum z (rel. intensity) 489 (M+H, 100). mp 186° C.

Example 12–14

3-(1-Amino-isoquinol-7-yl)-4-[(2'-aminosulfonyl-[1, 1']-biphen-4-yl)aminocarbonyl]-1,2,3-triazole (Example 12), 3-(4-Amino-isoquinol-7-yl)-4-[(2'-aminosulfonyl-[1,1']-biphen-4-yl)aminocarbonyl]-1, 2,3-triazole (Example 13), and 3-(isoquinol-7-yl)-4-[(2'-aminosulfonyl-[1,1']-biphen-4-yl) aminocarbonyl]-1,2,3-triazole (Example 14)

To a solution of 7-aminoisoquinoline (7.0 g) in TFA (35 mL) at 0° C. was added sodium nitrite (4.02 g) portionwise over a period of 30 minutes. The reaction was stirred at 0° C. to room temperature for 1.5 h. Water (3.5 mL) was added followed by portionwise addition of sodium azide (3.48 g) at 0° C. over a period of 30 minutes. After the addition, the reaction was slowly warmed up to room temperature and stirred for 1 h. Two third of TFA was evaporated and the residue was cooled to 0° C. Sodium bicarbonate (sat. in water) was added dropwisely to the residue until the pH was abouty 8–9. After extraction with methylene chloride (4×60 mL), the organic phase was combined, washed with water, brine, dried over sodium sulfate, filtered and concentrated to leave 7-azidoisoquinoline (7.5 g) as a dark brown solid. CI mass spectrum z (rel. intensity) 171 (M+H, 100).

7-Azidoisoquinoline (7.20 g) was suspended in toluene (80 mL). Propargyladehyde di-ethyl acetal (6.50 g) was added to the 7-azidoisoquinoline suspension. The reaction was stirred at room temperature overnight. The next day the solvent was evaporated and the residue was put on flash chromatography to give a mixture (10.25 g) of regioisomeric triazole aldehyde di-ethyl acetal in a 3:2 ratio by NMR. The mixture was further purified by recrystalization to give 1,2,3-triazole (6.50 g) as a pale yellow solid. CI mass spectrum z (rel. intensity) 299 (M+H, 100).

The acetal (1.5 g) was dissolved in TFA (50% in water, 15 mL). The resulting solution was stirred at room temperature overnight. The next day the solvent was evaporated and the residue was partitioned between ethyl acetate and sodium bicarbonate (sat. in water), washed with water, brine, dried over sodium sulfate, filtered and concentrated to give aldehyde (1.0 g) as a white solid. CI mass spectrum z (rel. intensity) 225 (M+H, 100).

To a solution of aldehyde (1.0 g) in methanol (25 mL) was added sodium cyanide (0.44 g), manganese (IV) oxide (6.30 g) and acetic acid (0.27 g). The reaction was stirred at room temperature overnight. The next day the reaction was filtered through celite, the pad was washed with a solution of methanol in methylene chloride (50%). The filtrate was concentrated and partitioned between ethylacetate and sodium bicarbonate (sat. in water), washed with water, dried over sodium sulfate, filtered and concentrated to give the carboxylate (0.75 g) as a pure compound. CI mass spectrum z (rel. intensity) 255 (M+H, 100).

To a solution of 2'-tert-butylaminosulfonyl-[1,1']-biphenyl-4-ylamine (132 mg) in methylene chloride (8 mL) was added AlMe$_3$ (2.0 M in hexane, 0.6 mL). The resulting solution was stirred at room temperature for 20 minutes. A solution of carboxylate (100 mg) in methylene chloride (5 mL) was added. The reaction was stirred at room temperature overnight. The next day the solvent was removed and HCl (10% in water, 5 mL) was added. The residue then was basified by the addition of sodium carbonate, partitioned between ethyl acetate and water, washed with sodium bicarbonate (sat. in water), water, dried over sodium sulfate, filtered and concentrated. Flash chromatography purification gave amide (110 mg) as a pure compound. ESI mass spectrum z (rel. intensity) 549 (M+Na, 100).

The amide (20 mg) was dissolved in TFA (2 mL). The resulting solution was stirred at 80° C. for 1 h. TFA was evaporated and the residue was purified on a flash chromatograpy to give 3-(isoquinol-7-yl)-4-[(2'-aminosulfonyl-[1,1']-biphen-4-yl)aminocarbonyl]-1,2,3-triazole (Example 14) as a pure compound. ESI mass spectrum z (rel. intensity) 471 (M+H, 100), mp 230° C.

To a suspension of triazole (80 mg) in methylene chloride (8 mL) was added MCPBA (50 mg). The reaction was stirred at reflux for 1 h. The mixture became a clear solution and was cooled to room temperature. The solvent was removed and the residue partitioned between ethylacetate and sodium bicarbonate (sat. in water), washed with water, dried over sodium sulfate, filtered and concentrated to give the desired isoquinoline-N-oxide (65 mg). To a solution of isoquinolne-N-oxide (65 mg) in pyridine (5 mL) was added TsCl (60 mg). The resulting solution was stirred at room temperature overnight. The next day the solvent was stripped off to dryness, ethanol amine (3 mL) was added. The reaction was stirred at room temperature overnight. The next day, the reaction mixture was partitioned between ethylacetate and water, the equeous phase was extracted with ethyl acetate (3×15 mL). The extracts were combined, concentrated and flash chromatographed to give the tert-butylaminosulfonyl compound (50 mg). The tert-butylaminosulfonyl compound (50 mg) was refluxed in TFA (4 mL) for 1 h and the TFA stripped off. The residue was partitioned between ethylacetate and sodium bicarbonate (sat. in water), washed with water, dried over sodium sulfate, filtered and concentrated, prep. TLC to give Example 12: 3-(1-amino-isoquinol-7-yl)-4-[(2'-aminosulfonyl-[1,1']-biphenyl-4-yl)aminocarbonyl]-1,2,3-triazole) (20 mg). ESI mass spectrum z (rel. intensity) 486 (M+H, 100), mp 250° C., and Example 13: 3-(4-amino-isoquinol-7-yl)-4-[(2'-aminosulfonyl-[1,1']-biphenyl-4-yl) aminocarbonyl]-1,2,3-triazole (6 mg). ESI mass spectrum z (rel. intensity) 486 (M+H, 100), mp 245° C.

Example 15

1-(Quinol-2-ylmethyl)-3-methyl-5-[(2'-aminosulfonyl-[1,1']-biphen-4-yl)aminocarbonyl]pyrazole The title compound was prepared analogously to Example 12. ESI mass spectrum z (rel. intensity) 484 (M+H, 100), mp 169° C.

Example 16

1-(Quinol-2-yl)-3-methyl-5-[(2'-aminosulfonyl-[1,1']-biphen-4-yl)aminocarbonyl]pyrazole The title compound was prepared analogously to Example 12. ESI mass spectrum z (rel. intensity) 484 (M+H, 100), mp 181° C.

Example 17

1-(3'-Aminoindazol-5'-yl)-3-methyl-5-[(2'-aminosulfonyl-[1,1']-biphen-4-yl)aminocarbonyl]pyrazole The title compound was prepared analogously to Example 12. ESI mass spectrum z (rel. intensity) 488 (M+H, 100), mp 203° C.

Example 18

1-(3-Aminoindazole-5-yl)-3-methyl-5-[(2'-aminosulfonyl-[1,1']-biphen-4-yl)aminocarbonyl]pyrazole The title compound was prepared analogously to Example 12. ESI mass spectrum z (rel. intensity) 488 (M+H, 100), mp 197° C.

Example 19

1-(3'-Aminobenzisoxazol-5'-yl)-3-methyl-5-[(2'-aminosulfonyl-(phenyl)pyridy-2-ylaminocarbonyl]pyrazole The title compound was prepared analogously to Example 12. ESI mass spectrum z (rel. intensity) 490 (M+H, 100), mp 188° C.

Example 20

1-(3'-Aminobenzisoxazol-5'-yl)-3-methyl-5-[isoquinol-7-yl)aminocarbonyl]pyrazole The title compound was prepared analogously to Example 12. ESI mass spectrum z (rel. intensity) 385 (M+H, 100), mp 210° C.

Example 21

1-(1'-Aminoisoquinol-7'-yl)-3-ethyl-5-[(2'-aminosulfonyl-[1,1']-biphen-4-yl)aminocarbonyl]pyrazole The title compound was prepared analogously to Example 12. ESI mass spectrum z (rel. intensity) 513 (M+H, 100), mp 201° C.

Example 22

1-(1'-Aminoisoquinol-7'-yl)-3-isopropyl-5-[(2'-aminosulfonyl-[1,1']-biphen-4-yl)aminocarbonyl]pyrazole The title compound was prepared analogously to Example 12. ESI mass spectrum z (rel. intensity) 527 (M+H, 100), mp 165° C.

Example 23

1-(2',4'-Diaminoquinazol-6'-yl)-3-methyl-5-[(2'-aminosulfonyl-[1,1']-biphen-4-yl)aminocarbonyl]pyrazole The title compound was prepared analogously to Example 12. ESI mass spectrum z (rel. intensity) 515 (M+H, 100), mp 215° C.

Example 24

1-(4'-Aminoquinazol-6'-yl)-3-methyl-5-[(2'-aminosulfonyl-[1,1']-biphen-4-yl)aminocarbonyl]pyrazole The title compound was prepared analogously to Example 12. ESI mass spectrum z (rel. intensity) 500 (M+H, 100), mp 205° C.

Example 25

1-(1'-Aminoisoquinol-7'-yl)-3-methyl-5-[4-(N-pyrrolidinylcarbonyl)phenylaminocarbonyl]pyrazole, trifluoroacetic acid salt Standard trimethylaluminum (Weinreb protocol) coupling of 4-carboxamidopyrrolidinophenyl-aniline with ethyl-N1-pyrazole(isoquinol-7-yl)-3-methyl-5-carboxylate, acidic workup and purification via silica gel column chromatography afforded the desired coupled product in 50% yield. $^1$H NMR (CDCl$_3$) δ: 9.20 (s, 1H), 8.89 (bs, 1H), 8.72 (d, 1H), 8.04 (s, 1H), 7.84 (d, 1H), 7.75 (dd, 1H), 7.66 (d, 1H), 7.45 (d, 2H), 7.37 (d, 2H), 6.80 (s, 1H), 3.60 (t, 2H), 3.39 (t, 2H), 2.40 (s, 1H), 1.84 (m-4H) ppm; ESI mass spectrum m/z (rel intensity) 426 (M+H, 100).

The isoquinoline product was then converted to the desired product following oxidation (MCPBA) and rearrangement (pTsCl/pyridine; ethanolamine) described previously. $^1$H NMR (DMSO d$_6$) δ: 8.70 (s, 1H), 7.98 (bs, 2H), 7.75 (dd, 4H), 7.46 (d, 2H), 7.27 (d, 1H), 7.09 (s, 1H), 3.30 (b, 4H), 2.34 (s, 3H), 7.78 (b, 4H) ppm; ESI mass spectrum m/z (rel intensity) 441 (M+H, 100).

Example 26

1-(3'-Aminobenzisoxazol-5'-yl)-3-trifluoromethyl-5-[(2'-methylsulfonyl-3-fluoro-[1,1']-biphen-4-yl)aminocarbonyl]pyrazole Preparation of 1-(4-Fluoro-3-cyanophenyl)-3-trifluoromethyl-5-pyrazolecarboxylic acid.

Method A

To a suspension of 4-fluoro-3-cyanophenylhydrazine tin chloride (20 g, 53.6 mmol) in ethanol (150 mL) was added 1,1,1-trifluoro-2,4-pentanedione (8.18 g, 53.6 mmol). The reaction was brought to reflux overnight. The next day the ethanol was evaporated and the residue partitioned between ethyl acetate and HCl (1 N). The aqueous phase was extracted with ethyl acetate (4×20 mL). The organic phase is washed with water, brine, dried over sodium sulfate, filtered and concentrated. Flash chromatography gave 1-(4-fluoro-3-cyanophenyl)-3-trifluoromethyl-5-methylpyrazole (8 g, 56% yield) as pure compound: MS (CI): 270 (M+H)$^+$ (100%).

To a solution of 1-(4-fluoro-3-cyanophenyl)-3-trifluoromethyl-5-methylpyrazole (4.0 g, 14.9 mmol) in CCl$_4$ (75 mL) was added NBS (5.3 g, 29.7 mmol) and benzylperoxide (0.2 g, 1.49 mmol). The reaction was brought to reflux overnight. The next day the CCl$_4$ was evaporated and the residue was partitioned between ethyl acetate and sodium bicarbonate (sat.). The organic phase was washed with water, brine, dried over sodium sulfate, filtered and concentrated. Flash chromatography gave 1-(4-fluoro-3-cyanophenyl)-3-trifluoromethyl-5-bromomethylpyrazole (2.6 g, 50% yield) as pure compound: MS (CI): 348 (M+H)$^+$ (100%).

To a solution of 1-(4-fluoro-3-cyanophenyl)-3-trifluoromethyl-5-bromomethylpyrazole (0.6 g, 1.72 mmol) in DMSO (10 mL) was added copper (I) oxide (0.52 g, 3.62 mmol) and water (3 mL). The reaction was stirred at 60° C. overnight. The next day the reaction mixture was filtered through Celite®. The filtrate was partitioned between ethyl acetate and water. The organic was washed three times with water, brine, dried over sodium sulfate, filtered and concentrated to leave 1-(4-fluoro-3-cyanophenyl)-3-trifluoromethyl-5-hydroxymethyl pyrazole (0.45 g, 92% yield) as pure compound: MS (CI): 286 (M+H)$^+$ (100%).

To a solution of 1-(4-fluoro-3-cyanophenyl)-3-trifluoromethyl-5-hydroxymethylpyrazole (0.45 g, 1.58 mmol) in acetonitrile (10 mL) was added catalytic amount of ruthenium chloride at 0° C. followed by addition of a solution sodium periodate (0.71 g, 3.32 mmol) in water. The reaction was stirred at 0° C. to room temperature overnight. The next day the acetonitrile was evaporated and the residue was partitioned between ethyl acetate and water, washed with brine, dried over sodium sulfate, filtered and concentrated to give 1-(4-fluoro-3-cyanophenyl)-3-trifluoromethyl-5-hydroxycarbonylpyrazole (0.27 g, 57% yield) as pure compound: MS (ES–): 298 (M–H)$^-$ (40%).

Method B

To a suspension of 4-fluoro-3-cyanophenylhyrazine tin chloride (17 g, 50 mmol) in acetic acid (200 mL) was added 4,4,4-trifluoro-1-(2-furyl)-2,4-butanedione (10.3 g, 50 mmol). The reaction was brought to reflux overnight. The next day the acetic acid was evaporated and the residue was partitioned between ethyl acetate and water, washed with HCl (1N), water and brine, dried over sodium sulfate, filtered and concentrated, flash chromatography to give 1-(4-fluoro-3-cyanophenyl)-3-trifluoromethyl-5-(2-furyl) pyrazole (7.0 g, 44% yield) as pure compound. MS (CI): 322 (M+H)$^+$ (100%).

To a solution of 1-(4-fluoro-3-cyanophenyl)-3-trifluoromethyl-5-(2-furyl)pyrazole (4.0 g, 12.5 mmol) in acetonitrile (30 mL) was added carbon tetrachloride (30 mL), ruthenium chloride (0.4 g) and a solution of sodium periodate (11.9 g, 56.1 mmol) in water (45 mL). The reaction is stirred at room temperature overnight. The next day the reaction mixture was filtered through celite. The filtrate was concentrated and partitioned between ethyl acetate and HCl (1N). The organic phase was washed with water, dried over sodium sulfate, filtered and concentrated to give 1-(4-fluoro-3-cyanophenyl)-3-trifluoromethyl-5-hydroxycarbonyl pyrazole (2.4 g, 64% yield) as pure compound. MS (ES–): 298 (M–H)$^-$ (40%).

Preparation of 1-(4-fluoro-3-cyanophenyl)-3-trifluoromethyl-5-[(2'-methylsulfonyl-3-fluoro-[1,1']-biphen-4-yl)aminocarbonyl]pyrazole.

To a solution of 1-(4-fluoro-3-cyanophenyl)-3-trifluoromethyl-5-hydroxycarbonylpyrazole (0.2 g, 0.67 mmol) in methylene chloride (10 mL) was added oxalyl chloride (0.84 g, 6.7 mmol) and one drop of DMF. The resulting solution was stirred at room temperature overnight.

The next day the solvent is evaporated and the residue is redissolved in methylene chloride and to the solution was added (2'-methylsulfonyl-3-fluoro-[1,1']-biphen-4-yl)amine hydrochloride (0.2 g, 0.67 mmol) and DMAP (0.25 g, 2.01 mmol). The reaction was stirred at room temperature overnight. The next day, methylene chloride was evaporated and the residue was partitioned between ethyl acetate and HCl (1N), washed with HCl (1N), sodium bicarbonate (sat.), brine and water, dried over sodium sulfate, filtered and concentrated to leave 1-(4-fluoro-3-cyanophenyl)-3-trifluoromethyl-5-[(2'-methylsulfonyl-3-fluoro-[1,1']-biphen-4-yl)aminocarbonyl]pyrazole (0.32 g, 87% yield) as pure compound. MS (ESI): 547 (M+H) (100%).
Preparation of 1-(3'-aminobenzisoxazol-5'-yl)-3-trifluoromethyl-5-[(2'-methylsulfonyl-3-fluoro-[1,1']-biphen-4-yl)aminocarbonyl]pyrazole To a solution of acetone oxime (86 mg, 1.18 mmol) in DMF (6 mL) was added sodium t-butoxide (1 M in THF, 1.18 mL). The mixture was stirred at room temperature for half hour followed by addition of a solution of 1-(4-fluoro-3-cyanophenyl)-3-trifluoromethyl-5-[(2'-methylsulfonyl-3-fluoro-[1,1']-biphen-4-yl)aminocarbonyl]pyrazole (0.22 g, 0.39 mmol) in DMF (4 mL). The reaction was stirred at room temperature for 5 hours. The reaction mixture was then partitioned between ethyl acetate and HCl (5%), washed with HCl (5%), four times with water, brine, dried over sodium sulfate, filtered and concentrated. Flash chromatography (30% ethyl acetate/hexane) gave 1-(4-isopropylideneaminooxy-3-cyanophenyl)-3-trifluoromethyl-5-[(2'-methylsulfonyl-3-fluoro-[1,1']-biphen-4-yl)aminocarbonyl]pyrazole (0.19 g, 81% yield) as pure compound: MS (ESI): 600 (M+H) (100%).

1-(4-Isopropylideneaminooxy-3-cyanophenyl)-3-trifluoromethyl-5-[(2'-methylsulfonyl-3-fluoro-[1,1']-biphen-4-yl)aminocarbonyl]pyrazole (0.19 g, 0.32 mmol) was dissolved in ethanol (4 mL) and to the solution was added HCl (20%, 4 mL). The reaction mixture was stirred at 80° C. for three hours. The reaction mixture was cooled to room temperature. The white precipitate was filtered and recrystalized in methanol to give the title compound (0.14 g, 80% yield): MS (ESI): 501 (M+H) (100%).

Example 27

1-(1'-Aminopthalazin-7'-yl)-3-methyl-5-[(2'-aminosulfonyl-[1,1']-biphen-4-yl)carbonylamino]pyrazole Preparation of 3-nitro-6-styrylbenzamide.

A mixture of 2-cyano-4-nitrotoluene (10 g, 6.17 mmol), benzaldehyde (6.51 g, 6.17 mmol) and potassium carbonate (20 g) in MeOH (200 mL) was heated at reflux for 10 min. The mixture was cooled to ambient temperature over 30 min, whereupon precipitation of the product was complete. The product was isolated by filtration and washed successively with 1N HCl, water and MeOH then air dried. There was obtained 13.0 g of the benzamide (mp 269.8° C.) as evident from the lack of a nitrile adsorption in the IR and the appearance of peaks at 3357.1, 3193.6 (—NH2) and 1648.7 cm$^{-1}$ (H2NC(=O)—); LRMS (M–NO)$^+$ m/z=238.
Preparation of 3-amino-6-styrylbenzamide.

The nitro compound prepared above (13 g, 48.41 mmol) and $SnCl_2.H_2O$ (54.7 g, 240 mmol) were combined in EtOH and heated at reflux for 1.5 h. The EtOH was removed by distillation in vacuo then 30% NaOH added. Extraction of this suspension with EtOAc followed by washing the organic extract with brine, drying ($MgSO_4$) and evaporation gave the product aniline (13.39 g); LRMS (M+H)$^+$ m/z=239.

Preparation of 3-hydrazino-6-styrylbenzamide.

The aniline (13 g, 54.6 mmol) from above was dissolved in conc. HCl (90 mL) and cooled to 0° C. A solution of $NaNO_2$ (3.94 g) in water (45 mL) was added dropwise over 10 min and the diazotization mixture left to stir at 0–5° C. for 1 h. After this time $SnCl_2.H_2O$ (39 g) in water (170 mL) was added dropwise to the cold mixture over 30 min then allowed to thaw to ambient temperature over 3 h. The solid product was isolated by filtration, then the filter cake was washed with water several times and air-dried to give the hydrazine contaminated with Sn (II) salts (10.9 g).
Preparation of ethyl 3-methyl-1-(3-amido-4-styrylphenyl)-1H-pyrazole-5-carboxylate.

The phenylhydrazine prepared above (3.2 g) and ethyl 2-N-(methoxy)imino-4-oxopentanoate (2.46 g, 13.18 mmol) in AcCN (30 mL) and AcOH (5 mL) were heated at reflux for 4 h. The reaction was cooled and diluted with EtOAc then washed repeatedly with satd. $NaHCO_3$ solution until the washings were basic. The mixture was evaporated and the dark oil left to stand until crystallization was complete. The solidified mass was triturated with 8:2 AcCN:water then filtered and air-dried. There was obtained 1.38 g of pyrazole; mp 162.6° C.; LRMS (M+H)+ m/z=376.
Preparation of ethyl 3-methyl-1-(3-cyano-4-styrylphenyl)-1H-pyrazole-5-carboxylate.

Ethyl 3-methyl-1-(3-amido-4-styrylphenyl)-1H-pyrazole-5-carboxylate (8.36 g, 22.3 mmol) in pyridine (50 mL) was cooled to 0° C. and methanesulfonyl chloride (7.67 g, 66.9 mmol) added dropwise over 10 min. The ice bath was removed and the reaction left to stir for 18 h. The reaction mixture was evaporated and the residue suspended in 1N HCl (200 mL) and MeOH (60 mL). The mixture was stirred vigourously for 15 min then filtered, washed with water and air-dried. There was obtained 6.23 g of nitrile; mp 128.3° C.
Preparation of 3-methyl-1-(3-cyano-4-styrylphenyl)-1H-pyrazole-5-carboxylic acid.

The ethyl ester (7.17 g, 20 mmol) in MeOH (100 mL) with 50% NaOH solution (10 mL) was stirred for 2 h at ambient temperature. After this time TLC (2:1 EtOAc:Hexane) indicated that all of the starting ester was consumed. Water (100 mL) was added and the solution acidified (pH=1) by the addition of conc. HCl. The percipitated product was removed by filtration then washed with water and air-dried. There was obtained 3-methyl-1-(3-cyano-4-styrylphenyl)-1H-pyrazole-5-carboxylic acid (5.9 g); mp 225.9° C.

To 3-methyl-1-(3-cyano-4-styrylphenyl)-1H-pyrazole-5-carboxylic acid (5.6 g, 17 mmol) in $CHCl_3$ (60 mL) and oxalyl chloride (3 mL) was added a few drops DMF. The reaction bubbled vigorously and after 20 min, when the reaction had subsided, the solvent was removed by distillation in vacuo and pumped on for several hours to remove the last traces of HCl. Complete conversion to the acid chloride was demonstrated by TLC (2:1 EtOAc:Hexane) by converting a small sample to the ethyl ester by treatment with EtOH and comparison with a previously prepared sample.

To the acid chloride (17 mmol) in CHCl3 (100 mL) and pyridine (170 mmol) was added 4-(2'-N-t-butylsulfamido)phenyl)aniline (5.2 g, 17.1 mmol). The reaction was stirred for 1 h at ambient temperature, then diluted with 1:1 EtOAc:n-BuCl (300 mL) and washed with 1N HCl until washings were acidic. The organic solution was dried and evaporated to give 8.12 g of 3-methyl-1-(3-cyano-4-styrylphenyl)-1H-pyrazole-5-(N-(4-(2'-t-butylsulfamido)phenyl)phenyl)carboxyamide; mp 130.3° C.; LRMS (M+Na)$^+$ m/z=638.2.

Preparation of 3-methyl-1-(3-cyano-4-formylphenyl)-1H-pyrazole-5-(N-(4-(2'-t-butylsulfamido)phenyl)phenyl)-carboxyamide.

A MeOH (200 mL) solution of 3-methyl-1-(3-cyano-4-styrylphenyl)-1H-pyrazole-5-(N-(4-(2'-t-butylsulfamido) phenyl)phenyl)carboxyamide was cooled to −78° C. and saturated with a stream of ozone. The solution was then purged with a stream of N2 for 10 min and dimethylsulfide (3 mL) added. The mixture was allowed to come to ambient temperature than evaporated to dryness. The residue was dissolved in EtOAc, washed with water (4×) dried (MgSO$_4$) and evaporated. There was obtained 3.97 g of the aldehyde; LRMS (M+Na)$^+$ m/z=564.0.

Preparation of Example 27

The above prepared carboxyamide (0.42 g, 0.78 mmol) with hydrazine hydrate (0.15 g, 3 mmol) and AcOH (0.28 g, 4.68 mmol) in benzene (25 mL) were heated at reflux under a Dean Stark trap for 18 h. The benzene solution was cooled to ambient temperature and washed with water (3×) and dried (MgSO4) then evaporated. The residue was applied to a short column of flash silica and eluted with 1:1:0.078 EtOAc:Hexane:MeOH. The desired pthalazine product (0.1 g) was obtained in a mixture with 3-methyl-1-(3-amido-4-(formylhydrazone)phenyl)-1H-pyrazole-5-(N-(4-(2'-t-butylsulfamido)phenyl)phenyl)carboxyamide.

This mixture was heated at reflux with trifluoroacetic acid (10 mL) for 1 h, then evaporated. The mixture was separated by reverse phase hplc on a C18 column by eluting with a gradient of 20% AcCN:Water with 0.05% TFA to 100% AcCN with 0.05% TFA over 30 min. At 9.83 min 3-methyl-1-(3-amido-4-(formylhydrazone)phenyl)-1H-pyrazole-5-(N-(4-(2'-sulfamido)phenyl)phenyl)carboxyamide (14 mg) was eluted; HRMS (M+H)$^+$ found: 518.1634, calc.: 518.1610. At 10.76 min the target compound, example 27 (2.8 mg) was eluted; HRMS (M+H)$^+$ found: 500.1511, calc.: 500.1505.

Example 28

3-(3'-Aminobenzisoxazol-5'-yl)-5-[[5-[(2'-aminosulfonyl)phenyl]pyrid-2-yl]aminocarbonyl]-5-(methylsulfonylaminomethyl)isoxazoline Preparation of 3-(3-cyano-4-fluorophenyl)-5-(azidomethyl)-5-(carbomethoxy)isoxazoline 3-Cyano-4-fluorobenzaldehyde (5.00 g) and hydroxyamine hydrochloride (2.90 g, 1.25 Eq) were dissolved in ethanol (100 mL) and pyridine (100 mL). The mixture was stirred at RT under N$_2$ for 45 minutes. The solvents were removed and the brown oil was partitioned between ethyl acetate and water. The organic layer was washed with brine, dried over MgSO$_4$, and concentrated to give 3-cyano-4-fluorobenzaldehydeoxime (5.03 g). CI mass spectrum z (rel. intensity) 165 (M+H, 100).

Sodium azide (10.7 g) was added to a solution of methyl (2-bromomethyl)acrylate (20.0 g) in DMSO (200 mL). The mixture was stirred at RT under N$_2$ for 2 h. The reaction mixture was poured into water and extracted with ethyl acetate. The organic layer was washed with brine, dried over MgSO$_4$, and concentrated to give methyl (2-azidomethyl) acrylate (14.1 g).

To a solution of 3-cyano-4-fluorobenzaldoxime (4.30 g) in CH$_2$Cl$_2$ (150 mL) was added methyl (2-azidomethyl) acrylate (4.33 g). The mixture was cooled to 0° C. in an ice bath followed by dropwise addition of NaOCl (66 mL of 0.67 M aqueous solution) with vigorous stirring. After the addition, the reaction mixture was slowly warmed up to RT (2 h). The mixture was washed with water and brine, dried over sodium sulfate, and concentrated. The resulting solid was purified by chromatography on silica gel with CH$_2$Cl$_2$ to give 3-(3-cyano-4-fluorophenyl)-5-(azidomethyl)-5-(carbomethoxy)isoxazoline (2.45 g) as a pure compound. $^1$H NMR (CDCl$_3$) δ 7.97 (m, 1H), 7.88 (m, 1H), 7.31 (t, 1H), 3.87 (s, 3H), 3.87–3.46 (m, 4H) ppm; NH$_3$-CI mass spectrum z (rel. intensity) 321 [(M+NH$_4$)$^+$, 100].

Preparation of 3-(3-cyano-4-fluorophenyl)-5-(aminomethyl)-5-(carbomethoxy)isoxazoline, hydrochloride salt.

To a solution of 3-[3-cyano-4-fluorophenyl]-5-(azidomethyl)-5-(carbomethoxy)isoxazoline (2.14 g) in THF (50 mL) was added triethylphosphite (1.45 mL). The mixture was refluxed under N$_2$ for 5 h. The THF was removed, and the residue was dissolved in EtOAc and washed with water and brine. It was dried over MgSO$_4$ and concentrated to a yellow oil. This oil was then dissolved in 4N HCl in dioxane (30 mL) and refluxed for 4 h. The reaction mixture was cooled, and ether was added. The precipitate formed was filtered and dried to give 1.15 g of the hydrochloride salt. $^1$H NMR (DMSO) δ 8.36 (bs, 2H), 8.21 (m, 1H), 8.09 (m, 1H), 7.68 (t, 1H), 4.02–3.80 (m, 2H), 3.78 (s, 3H), 3.70–3.37 (m, 2H) ppm; ESI mass spectrum z (rel. intensity) 279.9 (M+H, 100).

Preparation of 3-(3-cyano-4-fluorophenyl)-5-(methylsulfonylaminomethyl)-5-(carbomethoxy) isoxazoline.

To a solution of 3-(3-cyano-4-fluorophenyl)-5-(aminomethyl)-5-(carbomethoxy)isoxazoline hydrochloride salt (1.15 g) in CH$_2$Cl$_2$ (50 mL) was added triethylamine (1.27 mL) and methanesulfonyl chloride (0.31 mL). The mixture was stirred at RT under N$_2$ for 1 h. The solvent was diluted with CH$_2$Cl$_2$ and washed with water, 1N aqueous HCl, and saturated aqueous NaHCO$_3$. It was dried over MgSO$_4$ and concentrated to a yellow solid (1.13 g). $^1$H NMR (CDCl$_3$) δ 7.92 (m, 2H), 7.30 (t, 1H), 4.82 (t, 1H), 3.84 (s, 3H), 3.76–3.60 (m, 4H), 3.03 (s, 3H) ppm; ESI mass spectrum z (rel. intensity) 377.9 (M+H, 100).

Preparation of 3-(3-cyano-4-fluorophenyl)-5-(methylsulfonylaminomethyl)-5-(hydroxycarbonyl) isoxazoline.

To a solution of 3-(3-cyano-4-fluorophenyl)-5-(methylsulfonylaminomethyl)-5-(carbomethoxy) isoxazoline (1.13 g) in THF (50 mL) was added LiOH (3.50 mL of 1N aqueous solution). The mixture was stirred at RT under N$_2$ for ½ h. The solvent was removed, the resulting material was diluted with water and acidified with concentrated HCl. It was then extracted with EtOAc, and the organic solution was dried over MgSO$_4$ and concentrated to a light yellow foam (0.98 g). $^1$H NMR (DMSO-d$_6$) δ 8.17 (m, 2H), 7.56 (t, 1H), 3.98–3.79 (m, 2H), 3.69 (bs, 2H), 3.01 (s, 3H) ppm; ESI mass spectrum z (rel. intensity) 339.8 (M−H, 100).

Preparation of 3-(3-cyano-4-fluorophenyl)-5-[[5-[(2'-t-butylaminosulfonyl)phenyl]pyrid-2-yl]aminocarbonyl]-5-(methylsulfonylaminomethyl)isoxazoline.

To a solution of 3-(3-cyano-4-fluorophenyl)-5-(methylsulfonylaminomethyl)-5-(hydroxycarbonyl) isoxazoline (0.33 g) in CH$_3$CN (15 mL) was added oxalyl chloride (0.22 mL), followed by a few drops of DMF. The mixture was refluxed under N$_2$ for 1 h. The solvent was removed, toluene was added and then removed to dryness. The resulting solid was dried under vacuum. It was then dissolved in CH$_2$Cl$_2$ (20 mL) and [2-(t-butylaminosulfonyl) phenyl]-2-aminopyridine (0.30 g) was added followed by DMAP (0.30 g). The resulting mixture was stirred at RT under N₂ for 16 h. It was diluted with $CH_2Cl_2$ and washed with water and brine, dried over $MgSO_4$, and concentrated. The resulting solid was purified by chromatography on silica gel with 1:1 EtOAc/$CH_2Cl_2$ to give 0.11 g of the desired product. ¹H NMR (CDCl₃) δ 9.43 (s, 1H), 8.40 (d, 1H), 8.25 (d, 1H), 8.17 (dd, 1H), 7.98–7.83 (m, 3H), 7.62–7.50 (m, 2H), 7.35–7.24 (m, 2H), 5.81 (t, 1H), 4.06 (s, 1H), 3.82 (m, 4H), 3.02 (s, 3H), 1.07 (s, 9H) ppm; ESI mass spectrum z (rel. intensity) 629.0 (M+H, 100).

Preparation of 3-(3'-Aminobenzisoxazol-5'-yl)-5-[[5-[(2'-aminosulfonyl)phenyl]pyrid-2-yl]aminocarbonyl]-5-(methylsulfonylaminomethyl)isoxazoline To a solution of acetone oxime (28.0 mg) in DMF (2 mL) was added potassium tert-butoxide (1.0 M in THF, 0.44 mL) via syringe. The mixture was stirred at RT for 15 minutes, a solution of 3-(3-cyano-4-fluorophenyl)-5-[[5-[(2'-t-butylaminosulfonyl)phenyl]pyrid-2-yl]aminocarbonyl]-5-(methylsulfonylaminomethyl)isoxazoline (0.16 g) in DMF (2 mL) was added. The reaction mixture was stirred at RT overnight. Aqueous $NH_4Cl$ was added to quench the reaction solution. The mixture was poured into water and extracted with EtOAc. The organic solution was washed with brine, dried over $MgSO_4$, and concentrated to an oil.

This oil was dissolved in ethanol (8 mL) and methanol (2 mL). Aqueous HCl (18%, 2 mL) was added. The mixture was heated at 80° C. for 2 h. The solvents were removed and the residue was dissolved in $CH_3CN$ and purified by HPLC (C18 reverse phase, eluted with 0.05% of TFA in $H_2O$/$CH_3CN$) to give 50 mg of white solid as TFA salt. ESI mass spectrum z (rel. intensity) 641.9 (M+H, 100).

The above solid was refluxed with 5 mL of TFA under N₂ for 1/2 h. The solvents were removed and the residue was dissolved in $CH_3CN$ and purified by HPLC (C18 reverse phase, eluted with 0.05% of TFA in $H_2O$/$CH_3CN$) to give 31 mg of white solid as TFA salt. ¹H NMR (DMSO-d₆) δ 9.43 (s, 1H), 8.40 (d, 1H), 9.82 (s, 1H), 8.34 (d, 1H), 8.25 (s, 1H), 8.12–8.02 (m, 2H), 7.95–7.84 (in, 2H), 7.70–7.51 (m, 2H), 7.38 (m, 2H), 3.98–3.50 (m, 4H), 2.98 (s, 3H) ppm. ESI mass spectrum z (rel. intensity) 585.8 (M+H, 100).

Example 29

1-(3'-Aminobenzisoxazol-5'-yl)-3-trifluoromethyl-5-[(2-fluoro-4-morpholinophenyl)aminocarbonyl]pyrazole Preparation of 2-fluoro-4-morpholinoaniline.

A solution of 2,4-difluoronitrobenzene (10.0 mL) and morpholine (17.4 mL) in THF (100 mL) was stirred at RT under N₂ for 2 h. The solvent was removed and the residue was partitioned between EtOAc and water. The organic layer was washed brine, dried over $MgSO_4$, and concentrated. The resulting solid was purified by chromatography on silica gel with 20–50% EtOAc in hexane to give 18.1 g of 4-fluoro-2-morpholinonitrobenzene and 1.81 g of 2-fluoro-4-morpholinonitrobenzene. ESI mass spectrum z (rel. intensity) 227.1 (M+H, 100).

2-Fluoro-4-morpholinonitrobenzene (1.80 g) was dissolved in methanol (100 mL) and 10% Pd/C (94 mg) was added. The reaction mixture was placed in a hydrogenator (45 psi) for 2.5 h. The reaction mixture was filtered through celite and washed with methanol. The filtrate was concentrated to give 1.51 g solid. ¹H NMR (CDCl₃) δ 6.76–6.54 (m, 3H), 3.84 (t, 4H), 3.45 (bs, 2H), 3.02 (t, 4H) ppm. ESI mass spectrum z (rel. intensity) 197.1 (M+H, 100).

Preparation of 1-(3'-Aminobenzisoxazol-5'-yl)-3-trifluoromethyl-5-[(3-fluoro-4-morpholinophenyl)-aminocarbonyl]pyrazole.

The title compound was prepared from 1-(3-cyano-4-fluorophenyl)-3-trifluoromethyl-5-pyrazolecarboxylic acid and 2-fluoro-4-morpholinoaniline as a TFA salt by the same procedures described in Example 26. ¹ H NMR (DMSO-d₆) δ 9.39 (s, 1H), 8.06 (d, 1H), 7.77–7.48 (m, 4H), 6.81–6.75 (m, 2H), 3.77 (t, 4H), 3.15 (t, 4H) ppm. ESI mass spectrum z (rel. intensity) 491.2 (M+H, 100).

Example 30

1-(3'-Aminobenzisoxazol-5'-yl)-3-trifluoromethyl-5-[[4-(2'-isopropylimidazol-1'-yl)phenyl]aminocarbonyl]pyrazole The title compound was prepared in an analogous fashion as TFA salt. ¹H NMR (DMSO-d₆) δ 10.03 (s, 1H), 8.08 (d, 1H), 8.00 (d, 2H), 7.79–7.56 (m, 7H), 3.28 (m, 1H), 1.39 (d, 6H) ppm. ESI mass spectrum z (rel. intensity) 496.3 (M+H, 100).

Example 31

1-(3'-Aminobenzisoxazol-5'-yl)-3-trifluoromethyl-5-[[4-(2'-ethylimidazol-1'-yl)phenyl]aminocarbonyl]pyrazole The title compound was prepared in an analogous fashion as TFA salt. ¹H NMR (DMSO-d₆) δ 10.48 (s, 1H), 8.08 (d, 1H), 8.00 (d, 2H), 7.79–7.56 (m, 7H), 3.00 (q, 2H), 1.29 (t, 3H) ppm. ESI mass spectrum z (rel. intensity) 482.2 (M+H, 100).

Example 32

1-(3'-Aminobenzisoxazol-5'-yl)-3-trifluoromethyl-5-[[4-[(2'-dimethylaminomethyl)imidazol-1'-yl]phenyl]aminocarbonyl]pyrazole Preparation of 4-[(2'-dimethylaminomethyl)imidazol-1'-yl]aniline.

To a solution of 4-fluoronitrobenzene (7.87 g) and 2-imidazole-carboxaldehyde (5.90 g) in DMF (60 mL) was added $K_2CO_3$ (9.26 g). The mixture was heated at 80° C. under N₂ for 16 h. The mixture was poured into water, and the precipitate was filtered to give 6.70 g of yellow solid. The filtrate was then extracted with EtOAc, and the organic layer was washed brine, dried over $MgSO_4$, and concentrated to a yellow solid (5.40 g). Both batch were identified as the 4-[(2'-carboxaldehyde)imidazol-1'-yl]nitrobenzene. ESI mass spectrum z (rel. intensity) 218 (M+H, 100).

A mixture of 4-[(2'-carboxaldehyde)imidazol-1'-yl]nitrobenzene (3.00 g) and dimethylamine (32 mL of 40% aqueous solution) in methanol (50 mL) was stirred at RT under N₂ for ½ h. $NaBH_4$ (1.56 g) was added portion wise. After the addition was completed, the reaction mixture was heated at 56° C. for 2 h. Brine was added to the reaction mixture, it was then extracted with $CH_2Cl_2$. The organic solution was washed with brine, dried over $MgSO_4$, and concentrated to give 1.96 g of 4-[(2'-dimethylaminomethyl)imidazol-1'-yl]nitrobenzene. ESI mass spectrum z (rel. intensity) 247.2 (M+H, 100).

4-[(2'-dimethylaminomethyl)imidazol-1'-yl]nitrobenzene (1.96 g) was dissolved in methanol (100 mL) and 10% Pd/C (0.20 g) was added. The mixture was placed in a hydrogenator (30 psi) for 12 h. The reaction mixture was filtered through celite and washed with methanol. The filtrate was concentrated. It was then purified by chromatography on silica gel with 20% methanol in $CH_2Cl_2$ to give 1.30 g of 4-[(2'-dimethylaminomethyl)imidazol-1'-yl]aniline. $^1$H NMR ($CDCl_3$) δ 7.25 (dd, 2H), 7.03 (d, 2H), 6.72 (d, 2H), 3.82 (bs, 2H), 3.36 (s, 2H), 2.24 (s, 6H) ppm. ESI mass spectrum z (rel. intensity) 217.2 (M+H, 100).

Preparation of 1-(3'-Aminobenzisoxazol-5'-yl)-3-trifluoromethyl-5-[[4-[(2'-dimethylaminomethyl)imidazol-1'-yl]phenyl]aminocarbonyl]pyrazole The title compound was prepared from 1-(3-cyano-4-fluorophenyl)-3-trifluoromethyl-5-pyrazolecarboxylic acid and 4-[(2'-dimethylaminomethyl)imidazol-1'-yl]aniline as a TFA salt by the same procedures described in Example 26. $^1$H NMR (acetone-$d_6$) δ 10.39 (s, 1H), 8.07 (d, 1H), 7.93 (d, 2H), 7.76 (m, 1H), 7.56 (m, 5H), 7.36 (d, 1H), 4.59 (s, 2H), 3.00 (s, 6H), ppm. ESI mass spectrum z (rel. intensity) 511.2 (M+H, 100).

Example 33

1-(3'-Aminobenzisoxazol-5'-yl)-3-trifluoromethyl-5-[[4-[(2'-methoxymethyl)imidazol-1'-yl]phenyl] aminocarbonyl]pyrazole Preparation of 4-(2'-methoxymethyl)imidazol-1'-yl]aniline 4-[(2'-Carboxaldehyde)imidazol-1'-yl]nitrobenzene (3.00 g) was dissolved in methanol (50 mL). $NaBH_4$ (1.56 g) was added portion wise. After the addition was completed, the reaction mixture was stirred at RT under $N_2$ for 12 h. The methanol was removed and water was added. The precipitate formed was filtered and dried to give 1.90 g of 4-[(2'-hydroxymethyl)imidazol-1'-yl]nitrobenzene. $^1$H NMR (DMSO-$d_6$) δ 8.39 (d, 2H), 7.91 (d, 2H), 7.58 (s, 1H), 7.06 (s, 1H), 5.60 (t, 1H), 4.48 (d, 2H). AP z (rel. intensity) 220.1 (M+H, 100).

4-[(2'-hydroxymethyl)imidazol-1'-yl]nitrobenzene (1.70 g) was dissolved in $CH_2Cl_2$. Triethylamine (1.62 mL) was added followed by methanesulfonyl chloride (0.76 mL). The mixture was stirred at RT under $N_2$ for 2.5 h. The solvent was removed. The residue was dissolved in methanol (100 mL) and NaOMe (10 mL of 20% solution in methanol) was added. The reaction mixture was stirred at RT under $N_2$ for 12 h. The solvent was removed. The residue was partitioned between water and $CH_2Cl_2$. The organic solution was washed with brine, dried over $MgSO_4$, and concentrated to give 1.60 g of 4-[(2'-methoxymethyl)imidazol-1'-yl] nitrobenzene. $^1$H NMR ($CDCl_3$) δ 8.39 (d, 2H), 7.72 (d, 2H), 7.20 (s, 2H), 4.45 (s, 2H), 3.42 (s, 3H). ESI mass spectrum z (rel. intensity) 234.1 (M+H, 100).

4-[(2'-Methoxymethyl)imidazol-1'-yl]nitrobenzene (1.78 g) was dissolved in methanol (100 mL) and 10% Pd/C (0.20 g) was added. The mixture was placed in a hydrogenator (40 psi) for 20 h. The reaction mixture was filtered through celite and washed with methanol. The filtrate was concentrated. It was then purified by chromatography on silica gel with 5% methanol in $CH_2Cl_2$ to give 0.67 g of 4-[(2'-methoxymethyl) imidazol-1'-yl]aniline. $^1$H NMR ($CDCl_3$) δ 7.18 (d, 2H), 7.06 (d, 2H), 6.71 (d, 2H), 4.36 (s, 2H), 3.96 (bs, 2H), 3.35 (s, 3H) ppm. ESI mass spectrum z (rel. intensity) 204.2 (M+H, 100).

Preparation of 1-(3'-Aminobenzisoxazol-5'-yl)-3-trifluoromethyl-5-[[4-[(2'-methoxymethyl)imidazol-1'-yl] phenyl]aminocarbonyl]pyrazole.

The title compound was prepared from 1-(3-cyano-4-fluorophenyl)-3-trifluoromethyl-5-pyrazolecarboxylic acid and 4-[(2'-methoxymethyl)imidazol-1'-yl]aniline as a TFA salt by the same procedures described in Example 26. $^1$H NMR (acetone-$d_6$) δ 10.39 (s, 1H), 8.08 (d, 1H), 7.97 (d, 2H), 7.76 (m, 2H), 7.69 (m, 3H), 7.57 (m, 2H), 4.75 (s, 2H), 3.36 (s, 3H), ppm. ESI mass spectrum z (rel. intensity) 498.2 (M+H, 100).

Example 34

1-(3'-Aminobenzisoxazol-5'-yl)-3-trifluoromethyl-5-[[4-[(2'-dimethylaminomethyl)imidazol-1'-yl]-2-fluorophenyl]aminocarbonyl]pyrazole Preparation of 4-[(2'-dimethylaminomethyl)imidazol-1'-yl]-2-fluoroaniline.

2-Imidazole-carboxaldehyde (1.00 g) and dimethylamine (10 mL of 40% aqueous solution) in methanol (10 mL) was stirred at RT under $N_2$ for 1/2 h. $NaBH_4$ (1.18 g) was added portion wise. After the addition was completed, the reaction mixture was heated at 56° C. for 2 h. Brine was added to the reaction mixture, it was then extracted with $CH_2Cl_2$. The organic solution was washed with brine, dried over $MgSO_4$, and concentrated to 2-(dimethylaminomethyl)imidazole as a yellow oil. $^1$H NMR ($CDCl_3$) δ 6.97 (s, 2H), 3.61 (s, 2H), 2.28 (s, 6H) ppm.

The above oil was dissolved in DMF (10 mL) and KO-t-Bu (10.5 mL of 1M solution in THF) was added. The mixture was stirred at RT under $N_2$ for ½ h. It was then added dropwise to a solution of 2,4-difluoronitrobenzene (1.14 mL) in DMF (10 mL). The resulting mixture was stirred at RT under $N_2$ for 2 h. The mixture was poured into water and extracted with EtOAc. The organic layer was washed brine, dried over $MgSO_4$, and concentrated to a yellow oil. The resulting material was purified by chromatography on silica gel with EtOAc to give 1.11 g of a 1:5 mixture of 2-fluoro-4-[(2'-dimethylaminomethyl)imidazol-1'-yl]nitrobenzene and 4-fluoro-2-[(2'-dimethylaminiomethyl)imidazol-1'-yl]nitrobenzene. ESI mass spectrum z (rel. intensity) 265.2 (M+H, 100).

The above mixture was dissolved in methanol (100 mL) and 10% Pd/C (0.15 g) was added. The mixture was placed in a hydrogenator (40 psi) for 8 h. The reaction mixture was filtered through celite and washed with methanol. The filtrate was concentrated. The two regioisomers were then separated by HPLC (C18 reverse phase, eluted with 0.05% TFA in $H_2O/CH_3CN$) to give 80 mg of 4-[(2'-dimethylaminomethyl)imidazol-1'-yl]-2-fluoroaniline and 0.48 g of 2-[(2'-dimethylaminomethyl)imidazol-1'-yl]-4-fluoroaniline. ESI mass spectrum z (rel. intensity) 235.2 (M+H, 100).

Preparation of 1-(3'-Aminobenzisoxazol-5'-yl)-3-trifluoromethyl-5-[[4-[(2'-dimethylaminomethyl)imidazol-1'-yl]phenyl]aminocarbonyl]pyrazole.

The title compound was prepared from 1-(3-cyano-4-fluorophenyl)-3-trifluoromethyl-5-pyrazolecarboxylic acid and 4-[(2'-dimethylaminomethyl)imidazol-1'-yl]-2-fluoroaniline as a TFA salt by the same procedures described in Example 26. $^1$H NMR (acetone-$d_6$) δ 9.95 (s, 1H), 8.20–8.09 (m, 2H), 7.78 (m, 1 H), 7.59 (m, 4H), 7.44 (d, 1H), 7.36 (d, 1 H), 4.68 (s, 2H), 3.05 (s, 6H), ppm. ESI mass spectrum z (rel. intensity) 529.2 (M+H, 100).

TABLE 1

*Ring systems shown:*
- pyrazole-a (pzl-a)
- pyrazole-c (pzl-c)
- triazole (trz)
- pyrazole-b (pzl-b)
- isoxazoline (isox)
- tetrazole (tzl)

| Ex | D–E | Ring H | R$^{1a}$ | A–B | MS |
|---|---|---|---|---|---|
| 1 | 1'-Amino-isoquinol-7'-yl | pz1-a | Me | 2'—NH$_2$SO$_2$—[1,1']-biphen-4-yl | 499 |
| 2 | 1'-Amino-isoquinol-7'-yl | pz1-a | Me | 2'—CH$_3$SO$_2$—[1,1']-biphen-4-yl | 498 |
| 3 | 4'-amino-isoquinol-7'-yl | pz1-a | Me | 2'—NH$_2$SO$_2$—[1,1']-biphen-4-yl | 499 |
| 4 | isoquinol-7'-yl | pz1-a | Me | 2'—NH$_2$SO$_2$—[1,1']-biphen-4-yl | 484 |
| 5 | 1'-Amino-isoquinol-7'-yl | isox | Me | 2'—NH$_2$SO$_2$—[1,1']-biphen-4-yl | 502 |
| 6 | isoquinol-5'-yl | isox | Me | 2'—NH$_2$SO$_2$—[1,1']-biphen-4-yl | 487 |
| 7 | isoquinol-7'-yl | isox | Me | 2'—NH$_2$SO$_2$—[1,1']-biphen-4-yl | 487 |
| 8 | 2'-amino-benzimidazol-5'-yl | isox | Me | 2'—NH$_2$SO$_2$—[1,1']-biphen-4-yl | 491 |
| 9 | 3'-aminoindazol-5-yl | isox | Me | 2'—NH$_2$SO$_2$—[1,1']-biphen-4-yl | 491 |
| 10 | 3'-amino-benzisoxazol-5-yl | isox | Me | 2'—NH$_2$SO$_2$—[1,1']-biphen-4-yl | 492 |
| 11 | 3'-amino-benzisoxazol-5-yl | pz1-a | Me | 2'—NH$_2$SO$_2$—[1,1']-biphen-4-yl | 489 |
| 12 | 1'-Amino-isoquinol-7'-yl | trz | — | 2'—NH$_2$SO$_2$—[1,1']-biphen-4-yl | 486 |
| 13 | 4'-amino-isoquinol-7'-yl | trz | — | 2'—NH$_2$SO$_2$—[1,1']-biphen-4-yl | 486 |
| 14 | isoquinol-7'-yl | trz | — | 2'—NH$_2$SO$_2$—[1,1']-biphen-4-yl | 476 |
| 15 | quinol-2'-yl | pz1-a | Me | 2'—NH$_2$SO$_2$—[1,1']-biphen-4-yl | 484 |
| 16 | quinol-2'-yl | pz1-b | Me | 2'—NH$_2$SO$_2$—[1,1']-biphen-4-yl | 484 |
| 17 | 3'-amino-indazol-5-yl | pz1-a | Me | 2'—NH$_2$SO$_2$—[1,1']-biphen-4-yl | 488 |
| 18 | 3'-aminoindazol-5-yl | pz1-a | Me | 2'—NH$_2$SO$_2$—[1,1']-biphen-4-yl | 488 |
| 19 | 3'-amino-benzisoxazol-5-yl | pz1-a | Me | 5-(2'—NH$_2$SO$_2$—phenyl)pyrid-2-yl | 490 |
| 20 | 3'-amino-benzisoxazol-5-yl | pz1-a | Me | isoquin-7-yl | 385 |
| 21 | 1'-Amino-isoquinol-7'-yl | pz1-a | Et | 2'—NH$_2$SO$_2$—[1,1']-biphen-4-yl | 513 |
| 22 | 1'-Amino-isoquinol-7'-yl | pz1-a | i-Pr | 2'—NH$_2$SO$_2$—[1,1']-biphen-4-yl | 527 |

TABLE 1-continued

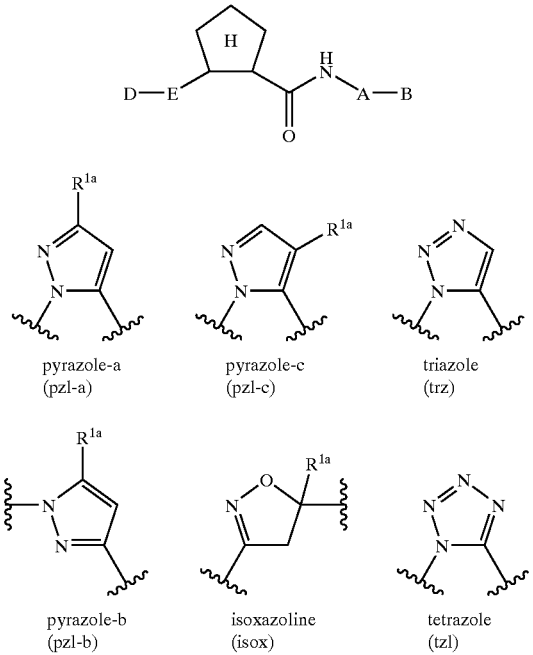

| Ex | D–E | Ring H | R1a | A–B | MS |
|---|---|---|---|---|---|
| 23 | 2',4'-diamino-quinazol-7'-yl | pzl-a | Me | 2'—NH$_2$SO$_2$—[1,1']-biphen-4-yl | 515 |
| 24 | 4'-amino-quinazol-7'-yl | pzl-a | Me | 2'—NH$_2$SO$_2$—[1,1']-biphen-4-yl | 500 |
| 25 | 1'-Amino-isoquinol-7'-yl | pzl-a | Me | 4-(N-pyrrolidinyl-carbonyl)phenyl | 441 |
| 26 | 3'-amino-benzisoxazol-5'-yl | pzl-a | CF$_3$ | 3-F-2'- CH$_3$SO$_2$-[1,1']-biphen-4-yl | 501 |
| 27 | 1'-Amino-pthalazin-7'-yl | pzl-a | CH$_3$ | 2'—NH$_2$SO$_2$-[1,1']-biphen-4-yl | 500 |
| 28 | 3'-amino-benzisoxazol-5'-yl | isox | CH$_3$SO$_2$NH—CH$_2$ | 5-(2'-NH$_2$SO$_2$-phenyl)pyrid-2-yl | 586 |
| 29 | 3'-amino-benzisoxazol-5'-yl | pzl-a | CF$_3$ | 2-F-4-morpholinophenyl | 491 |
| 30 | 3'-amino-benzisoxazol-5'-yl | pzl-a | CF$_3$ | 2'-iPr-imidazol-1'-ylphenyl | 496 |
| 31 | 3'-amino-benzisoxazol-5'-yl | pzl-a | CF$_3$ | 2'-Et-imidazol-1'-ylphenyl | 482 |
| 32 | 3'-amino-benzisoxazol-5'-yl | pzl-a | CF$_3$ | 2'-(CH$_3$)$_2$NCH$_2$-imidazol-1'-ylphenyl | 511 |
| 33 | 3'-amino-benzisoxazol-5'-yl | pzl-a | CF$_3$ | 2'-CH$_3$OCH$_2$-imidazol-1'-ylphenyl | 498 |
| 34 | 3'-amino-benzisoxazol-5'-yl | pzl-a | CF$_3$ | 2-F-2'-(CH$_3$)$_2$NCH$_2$-imidazol-1'-ylphenyl | 529 |

What is claimed is:

1. The compound entitled 1-(4-fluoro-3-cyanophenyl)-3-trifluoromethyl-5-pyrazolecarboxylic acid.

2. The compound entitled 1-(4-fluoro-3-cyanophenyl)-3-trifluoromethyl-5-(2-furyl)pyrazole.

3. The compound entitled 4-[(2'-dimethylaminomethyl)imidazol-1'-yl]-2-fluoroaniline.

* * * * *

UNITED STATES PATENT AND TRADEMARK OFFICE
CERTIFICATE OF CORRECTION

PATENT NO.   : 6,965,036 B2
DATED        : November 15, 2005
INVENTOR(S)  : Mimi L. Quan and Renhua Li It is certified that error appears in the above-identified patent and that said Letters Patent is hereby corrected as shown below:

<u>Title Page,</u>
Item [62], Related U.S. Application Data, delete "Division of application No. 09/924,381, filed on Aug. 8," and insert -- This is a Continuation of application No. 09/924,381, filed on Aug. 8, --.

Signed and Sealed this

Thirteenth Day of June, 2006

JON W. DUDAS
*Director of the United States Patent and Trademark Office*